(12) United States Patent
Hyman et al.

(10) Patent No.: US 9,220,870 B2
(45) Date of Patent: Dec. 29, 2015

(54) CATHETER SECUREMENT DEVICES

(71) Applicant: INSIGHTRA MEDICAL INCORPORATED, Irvine, CA (US)

(72) Inventors: Daniel Hyman, Irvine, CA (US); Wayne A. Noda, Irvine, CA (US); Stephen G. Bell, Irvine, CA (US)

(73) Assignee: Insightra Medical Incorporated, Irvine, CA (US)

( * ) Notice: Subject to any disclaimer, the term of this patent is extended or adjusted under 35 U.S.C. 154(b) by 58 days.

(21) Appl. No.: 14/233,257

(22) PCT Filed: Jan. 18, 2013

(86) PCT No.: PCT/US2013/022070
§ 371 (c)(1),
(2) Date: Jan. 16, 2014

(87) PCT Pub. No.: WO2013/109835
PCT Pub. Date: Jul. 25, 2013

(65) Prior Publication Data
US 2014/0163515 A1   Jun. 12, 2014

Related U.S. Application Data

(60) Provisional application No. 61/588,515, filed on Jan. 19, 2012, provisional application No. 61/652,589, filed on May 29, 2012.

(51) Int. Cl.
*A61M 5/32* (2006.01)
*A61M 25/02* (2006.01)

(52) U.S. Cl.
CPC ......... *A61M 25/02* (2013.01); *A61M 2025/024* (2013.01); *A61M 2025/026* (2013.01); *A61M 2025/028* (2013.01); *A61M 2025/0253* (2013.01)

(58) Field of Classification Search
CPC ............... A61M 2025/024; A61M 2025/0246; A61M 2025/0266; A61M 25/02; A61M 2025/0253; A61M 2025/026; A61M 2025/028
See application file for complete search history.

(56) References Cited

U.S. PATENT DOCUMENTS

| | | | |
|---|---|---|---|
| 4,129,128 A | 12/1978 | McFarlane |
| 4,366,817 A | 1/1983 | Thomas |
| 4,711,636 A | 12/1987 | Bierman |
| 5,192,273 A | 3/1993 | Bierman |

(Continued)

FOREIGN PATENT DOCUMENTS

| | | |
|---|---|---|
| AU | 2011202877 | 7/2011 |
| WO | 0162328 A1 | 8/2001 |
| WO | 2007082093 A2 | 7/2007 |

OTHER PUBLICATIONS

Daniel Hyman, Wayne A. Noda, Stephen G. Bell, "Catheter Securement Device" related U.S. Appl. No. 14/233,234, non-final office action dated Oct. 6, 2014.

(Continued)

*Primary Examiner* — Rebecca E Eisenberg
(74) *Attorney, Agent, or Firm* — John L. Rogitz

(57) ABSTRACT

Described herein are catheter securement devices that can be used to secure catheters, catheter hubs and other medical devices to the body of a patient. The catheter securement devices can include an adhesive pad and engagement tabs with a slide locking feature. Adaptors can be used to provide suture tabs to catheters that lack suture tabs.

19 Claims, 33 Drawing Sheets

(56) References Cited

U.S. PATENT DOCUMENTS

| | | |
|---|---|---|
| 5,192,274 A | 3/1993 | Bierman |
| 5,382,239 A | 1/1995 | Orr et al. |
| 5,456,671 A | 10/1995 | Bierman |
| 5,693,032 A | 12/1997 | Bierman |
| 5,702,371 A | 12/1997 | Bierman |
| 5,722,959 A | 3/1998 | Bierman |
| 5,800,402 A | 9/1998 | Bierman |
| 5,810,781 A | 9/1998 | Bierman |
| 6,132,398 A | 10/2000 | Bierman |
| 6,213,979 B1 | 4/2001 | Bierman |
| 6,224,571 B1 | 5/2001 | Bierman |
| 6,283,945 B1 | 9/2001 | Bierman |
| 6,290,676 B1 | 9/2001 | Bierman |
| 6,358,230 B1 | 3/2002 | Davey |
| 6,361,523 B1 | 3/2002 | Bierman |
| 6,413,240 B1 | 7/2002 | Bierman et al. |
| 6,428,516 B1 | 8/2002 | Bierman |
| 6,447,485 B2 | 9/2002 | Bierman |
| 6,491,664 B2 | 12/2002 | Bierman |
| 6,551,285 B1 | 4/2003 | Bierman |
| 6,582,403 B1 | 6/2003 | Bierman et al. |
| 6,663,600 B2 | 12/2003 | Bierman et al. |
| 6,689,104 B2 | 2/2004 | Bierman |
| 6,770,055 B2 | 8/2004 | Bierman et al. |
| 6,786,892 B2 | 9/2004 | Bierman |
| 6,929,625 B2 | 8/2005 | Bierman |
| 6,951,550 B2 | 10/2005 | Bierman |
| 6,979,320 B2 | 12/2005 | Bierman |
| 7,014,627 B2 | 3/2006 | Bierman |
| 7,018,362 B2 | 3/2006 | Bierman et al. |
| 7,153,291 B2 | 12/2006 | Bierman |
| 7,223,256 B2 | 5/2007 | Bierman |
| 7,247,150 B2 | 7/2007 | Bierman |
| 7,354,421 B2 | 4/2008 | Bierman |
| 7,520,870 B2 | 4/2009 | Bierman |
| 7,578,804 B2 | 8/2009 | Bierman |
| 7,591,803 B2 | 9/2009 | Bierman |
| 7,635,355 B2 | 12/2009 | Bierman |
| 7,651,479 B2 | 1/2010 | Bierman |
| 7,666,167 B2 | 2/2010 | Bierman |
| 7,785,295 B2 | 8/2010 | Bierman |
| 7,799,001 B2 | 9/2010 | Bierman |
| 7,806,873 B2 | 10/2010 | Dikeman et al. |
| 7,811,258 B2 | 10/2010 | Bierman |
| 7,837,655 B2 | 11/2010 | Bierman et al. |
| 7,879,013 B2 | 2/2011 | Smith et al. |
| 7,922,697 B2 | 4/2011 | Beran |
| 7,955,307 B2 | 6/2011 | Bierman et al. |
| 8,016,792 B2 | 9/2011 | Wright et al. |
| 8,016,793 B2 | 9/2011 | Wright et al. |
| 8,025,643 B2 | 9/2011 | Bierman |
| 8,052,648 B2 | 11/2011 | Dikeman et al. |
| 8,057,440 B2 | 11/2011 | Bierman |
| 8,100,862 B2 | 1/2012 | Bierman |
| 8,105,290 B2 | 1/2012 | Wright et al. |
| 8,211,063 B2 | 7/2012 | Bierman et al. |
| 8,241,253 B2 | 8/2012 | Bracken |
| 8,246,583 B2 | 8/2012 | Bierman |
| 8,251,956 B2 | 8/2012 | Bierman et al. |
| 8,282,606 B2 | 10/2012 | Bierman |
| 8,298,191 B2 | 10/2012 | Bierman et al. |
| 8,357,124 B2 | 1/2013 | Bierman |
| 8,394,065 B2 | 3/2013 | Bierman |
| 8,398,599 B2 | 3/2013 | Bierman |
| 8,475,408 B2 | 7/2013 | Mernoe et al. |
| 8,506,531 B2 | 8/2013 | Bierman |
| 8,540,680 B2 | 9/2013 | Burn |
| 8,608,704 B2 | 12/2013 | Bierman |
| 2002/0188257 A1 | 12/2002 | Bierman |
| 2005/0076921 A1* | 4/2005 | Rozier et al. ................ 128/877 |
| 2005/0192594 A1* | 9/2005 | Skakoon et al. ............. 606/129 |
| 2006/0276752 A1 | 12/2006 | Bierman et al. |
| 2007/0265571 A1 | 11/2007 | Utterberg et al. |
| 2007/0276334 A1 | 11/2007 | Bierman et al. |
| 2008/0132848 A1 | 6/2008 | Wright et al. |
| 2008/0171993 A1* | 7/2008 | Beran .......................... 604/180 |
| 2008/0221526 A1* | 9/2008 | Fleischer ..................... 604/180 |
| 2008/0243082 A1 | 10/2008 | Goodman |
| 2009/0093769 A1 | 4/2009 | Wright et al. |
| 2009/0143740 A1 | 6/2009 | Bierman et al. |
| 2009/0326474 A1 | 12/2009 | Bierman et al. |
| 2010/0114034 A1 | 5/2010 | Wright et al. |
| 2010/0324491 A1 | 12/2010 | Bierman et al. |
| 2011/0112483 A1 | 5/2011 | Smith et al. |
| 2011/0178467 A1 | 7/2011 | Bierman et al. |
| 2011/0245777 A1 | 10/2011 | Andino et al. |
| 2011/0257600 A1 | 10/2011 | Kessler |
| 2011/0264050 A1 | 10/2011 | Henry et al. |
| 2011/0282291 A1 | 11/2011 | Ciccone |
| 2011/0319830 A1 | 12/2011 | Peters et al. |
| 2012/0130315 A1 | 5/2012 | Weadock et al. |
| 2012/0136314 A1 | 5/2012 | Ciccone et al. |
| 2012/0197205 A1 | 8/2012 | Peters |
| 2012/0232490 A1 | 9/2012 | Andino |
| 2012/0265147 A1 | 10/2012 | Andino et al. |
| 2012/0271240 A1 | 10/2012 | Andino et al. |
| 2013/0018319 A1* | 1/2013 | Abe et al. ..................... 604/174 |
| 2013/0079721 A1* | 3/2013 | Mizoguchi et al. ........... 604/174 |
| 2013/0079722 A1* | 3/2013 | Makino et al. ............... 604/174 |

OTHER PUBLICATIONS

Daniel Hyman, Wayne A. Noda, Stephen G. Bell, "Catheter Securement Device" related U.S. Appl. No. 14/233,234, applicants response to non-final office action filed Nov. 9, 2014.

* cited by examiner

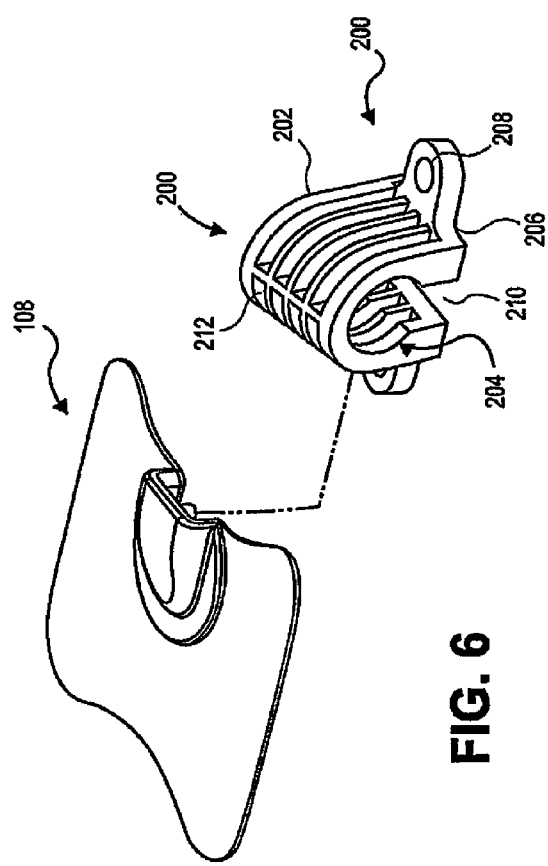
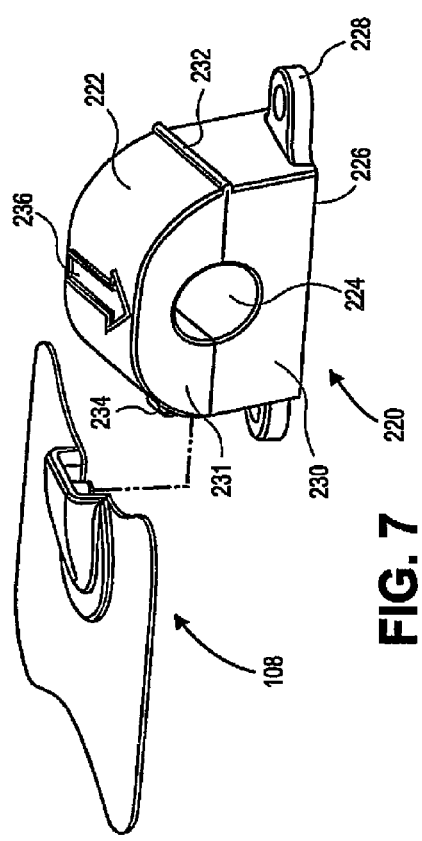

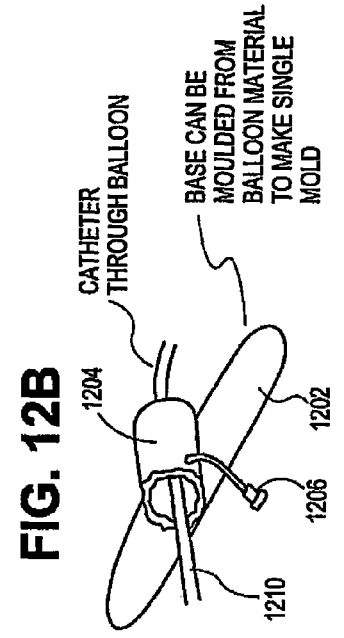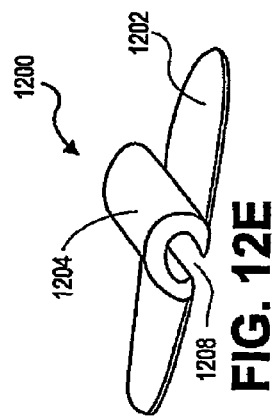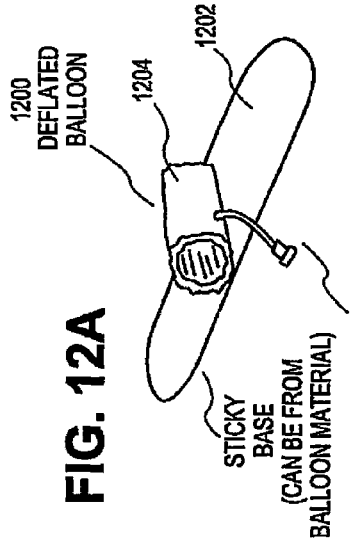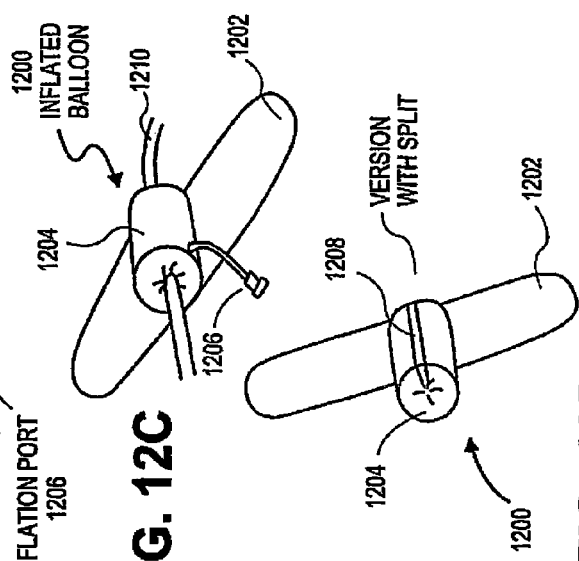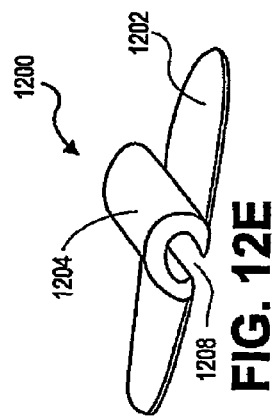

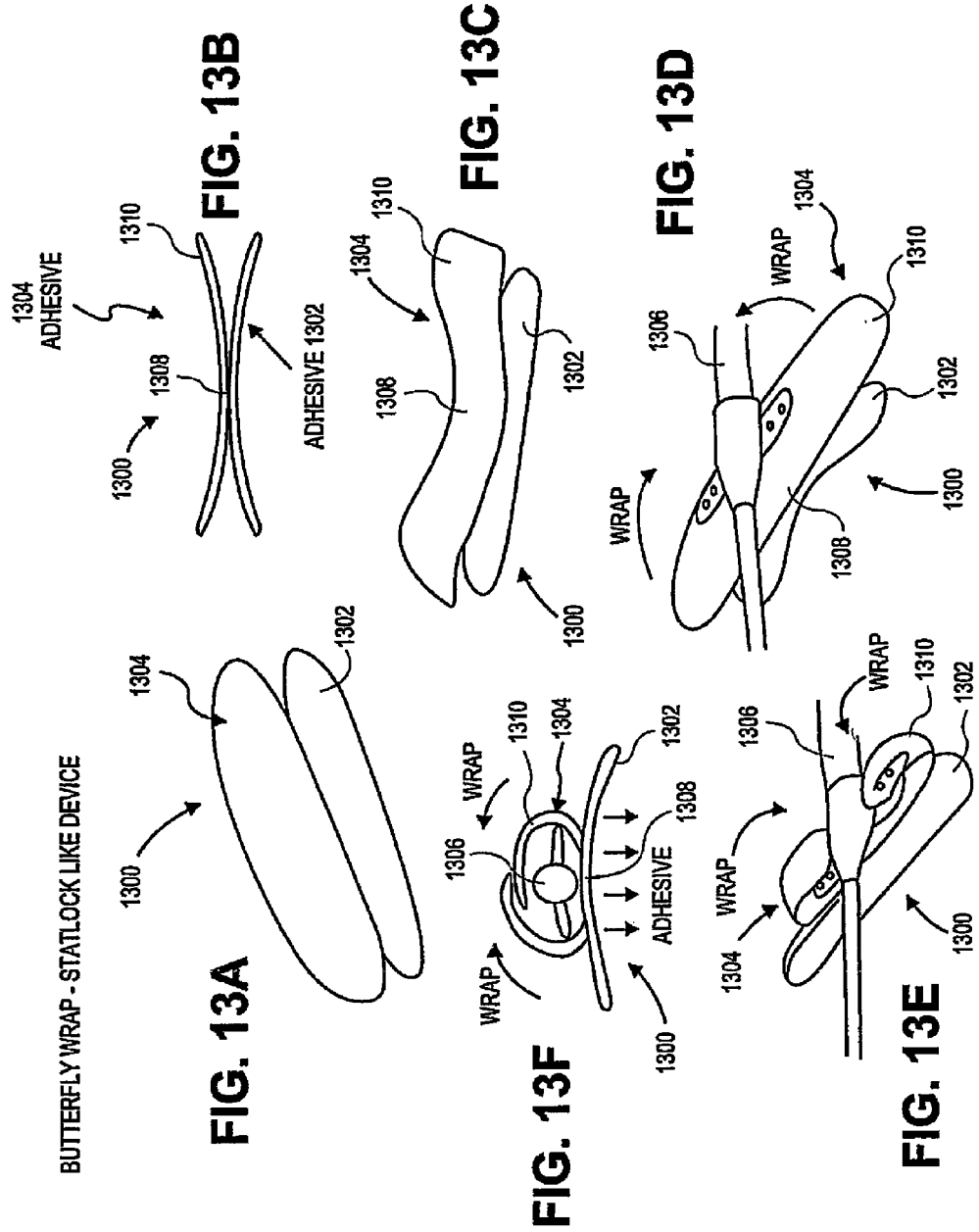

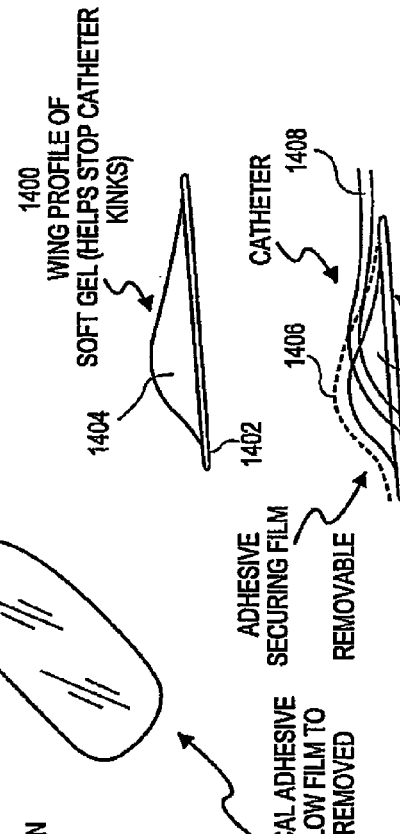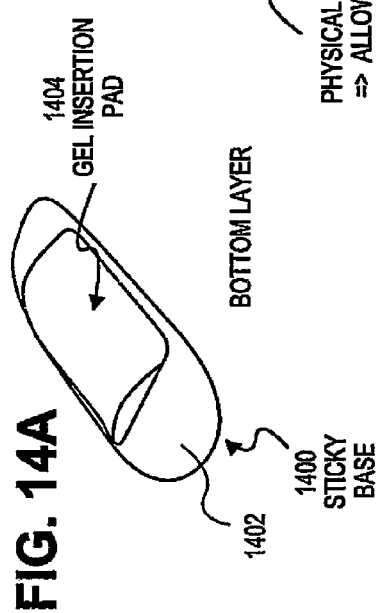

CATHETER SECUREMENT DEVICES

Vacuum formed Blister pack with adhesive overlay sticker with integrated tube management.

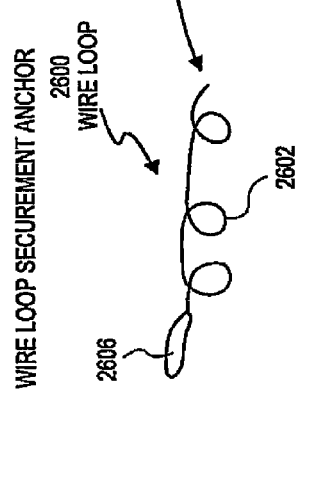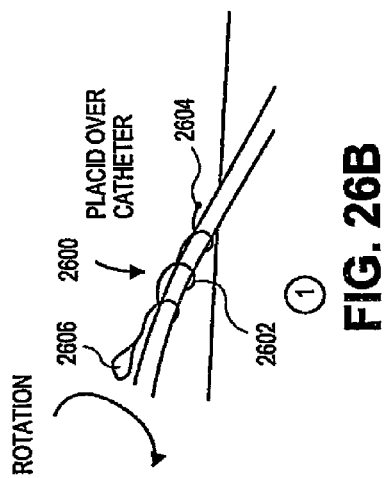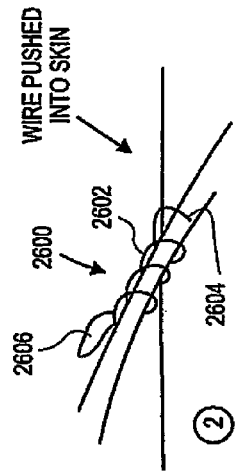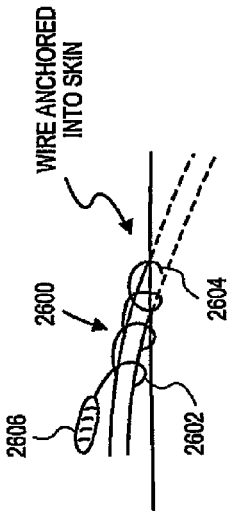

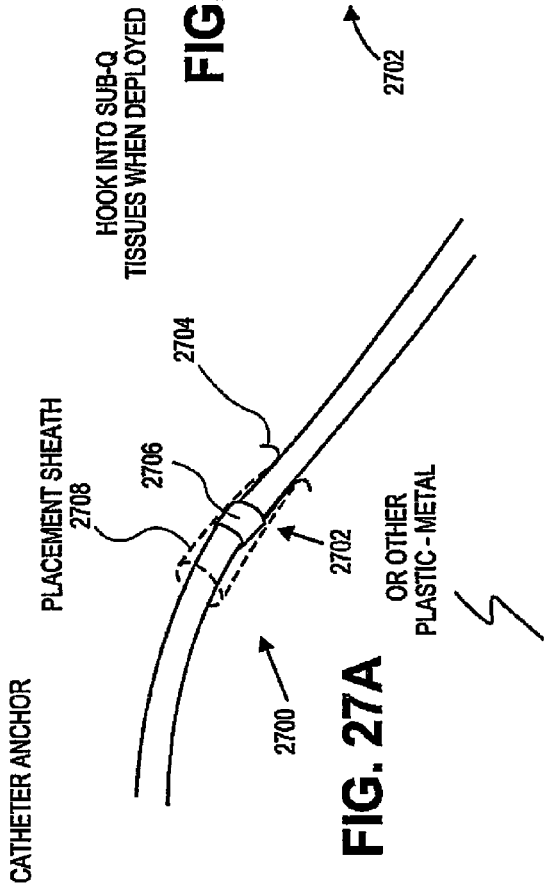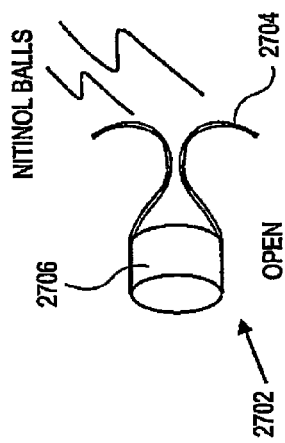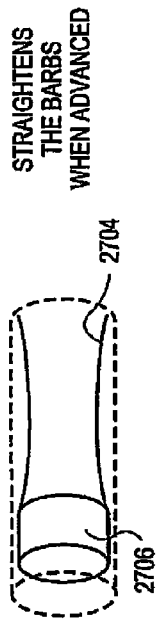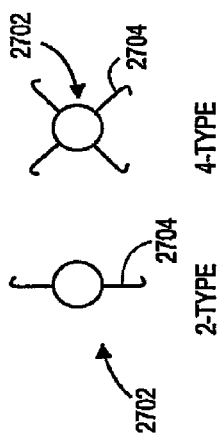

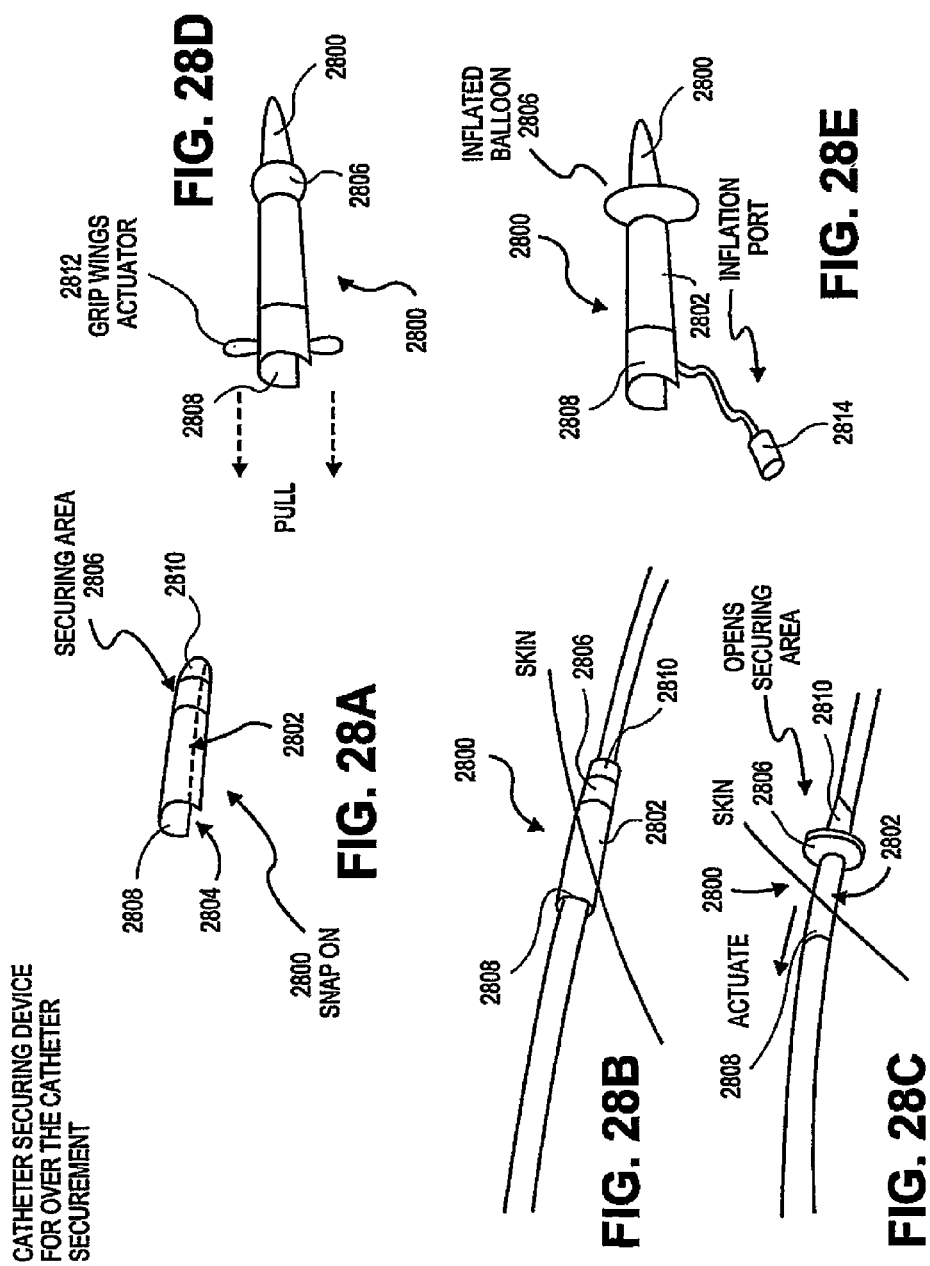

SUBCUTANEOUS EXPANDING ANCHOR

DOUBLE LOCKING CATHETER GRIP.
TO STOP IN AND OUT MOVEMENT.

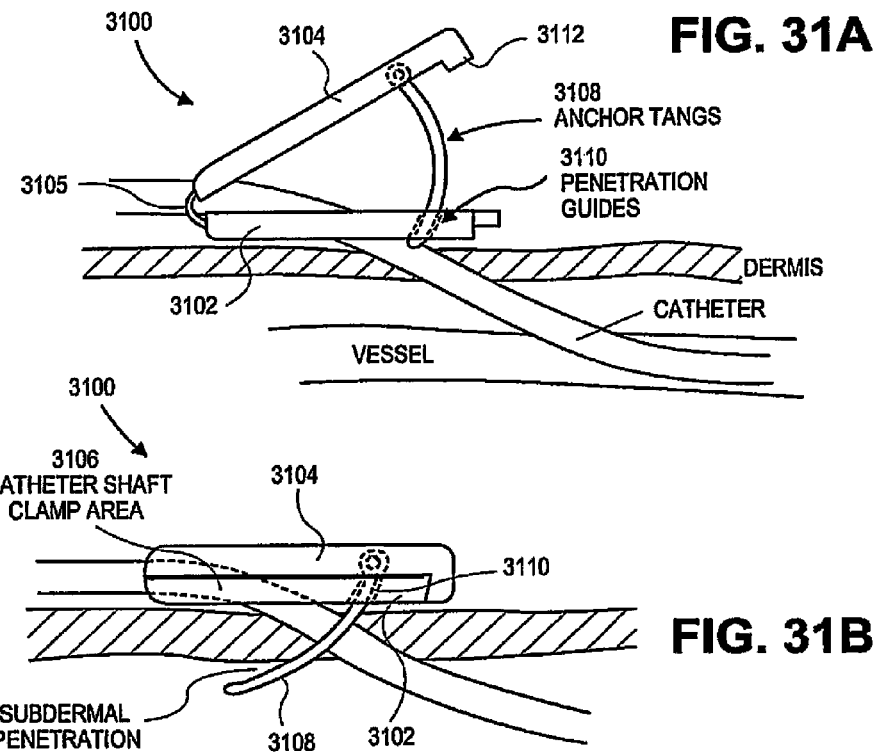
FIG. 31A
FIG. 31B
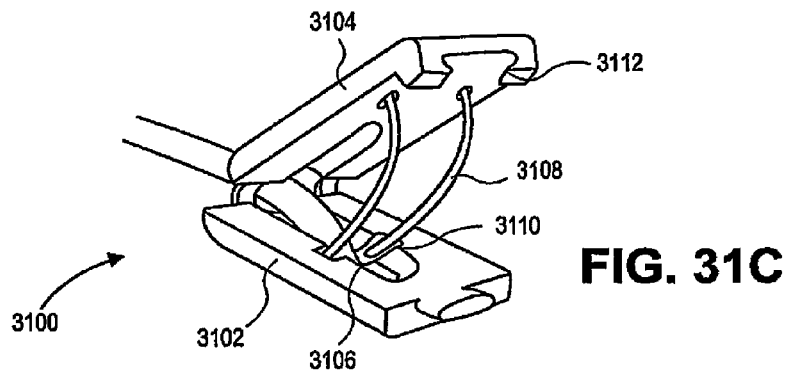
FIG. 31C

TOP VIEW

BOTTOM VIEW

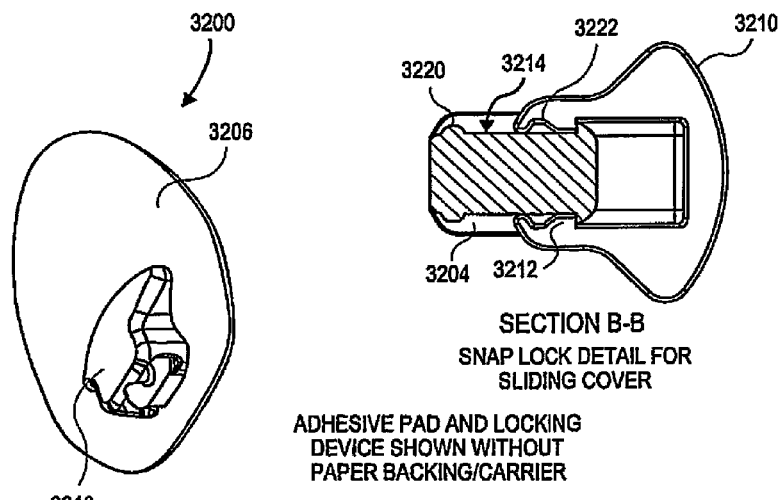
SECTION B-B
SNAP LOCK DETAIL FOR
SLIDING COVER
ADHESIVE PAD AND LOCKING
DEVICE SHOWN WITHOUT
PAPER BACKING/CARRIER
FIG. 32F
FIG. 32E
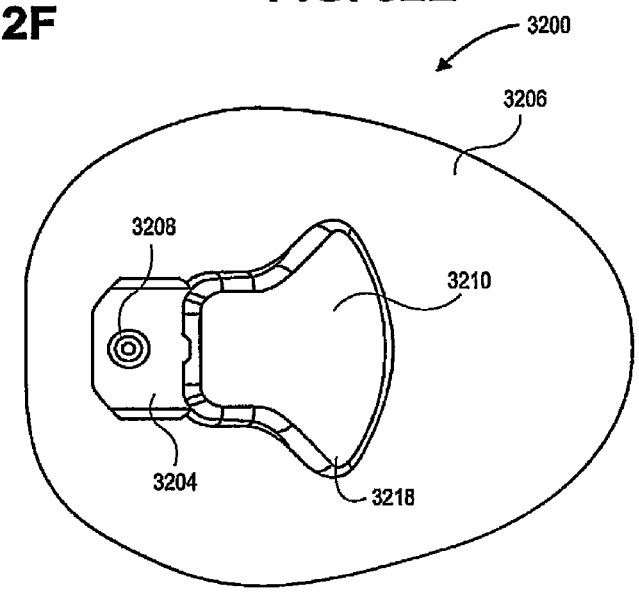
FIG. 32G

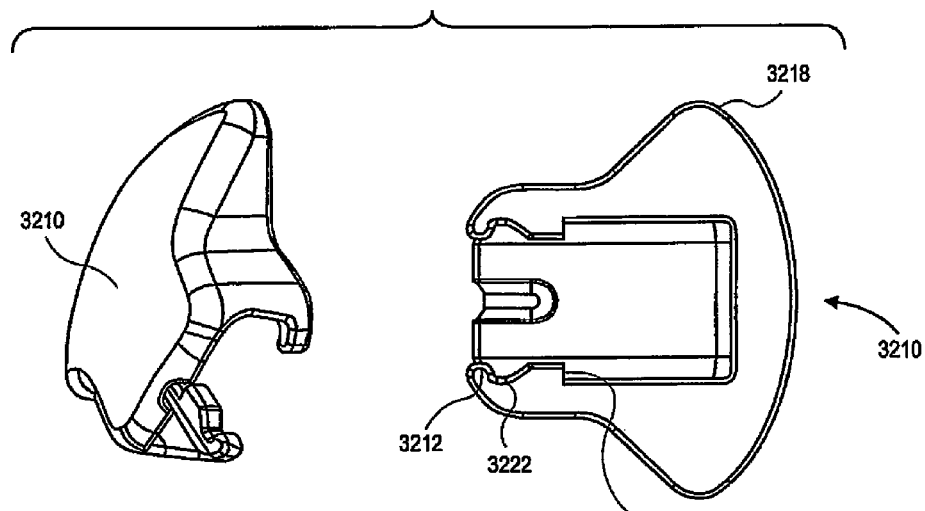
FIG. 32H  FIG. 32I
COVER COMPONENT
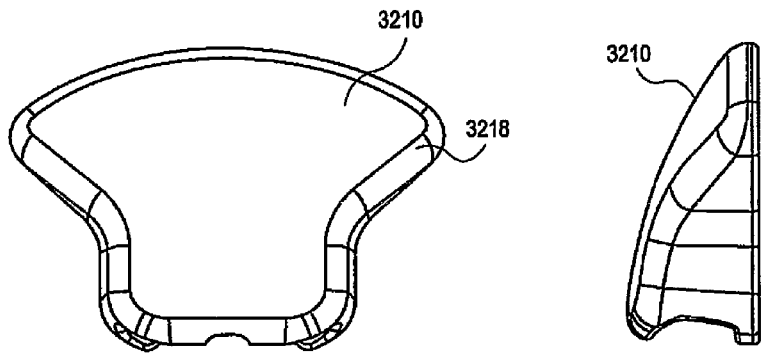
FIG. 32J  FIG. 32K

BASE COMPONENT

SECUREMENT DEVICE INSTALLED
ON CATHETER SUTURE TABS

CATHETER SECUREMENT DEVICES

CROSS REFERENCE TO RELATED APPLICATIONS

This application claims the benefit of U.S. Provisional Patent Application Ser. No. 61/588,515 entitled "Designs and Methods for Catheter Securement Devices" and filed Jan. 19, 2012, and U.S. Provisional Patent Application Ser. No. 61/652,589 entitled "Sliding Lock Devices for Catheter Securement" and filed May 29, 2012, all of which are hereby incorporated by reference for all purposes.

INCORPORATION BY REFERENCE

All publications and patent applications mentioned in this specification are herein incorporated by reference to the same extent as if each individual publication or patent application was specifically and individually indicated to be incorporated by reference.

FIELD

The inventions relate generally to devices for securing medical devices to a patient's body. More specifically, the inventions relate to devices for securing catheters, tubing or medical lines to a patient's skin.

BACKGROUND

Catheters, tubing and/or medical lines can be used to introduce fluids, medications or medical devices directly into the patient or to withdraw fluids from the patient. Often, it becomes desirable to maintain such catheterization over an extended period of time during the treatment of a patient. In order to keep the catheter, tubing or other medical line properly positioned for the duration of treatment, the catheter, tubing or medical line can be secured to the patient in a variety of ways. For example, the catheter, tubing or medical line can be taped to the patient.

Securing a catheter with tape upon the patient traditionally has certain drawbacks. The use of tape at the insertion site can retain dirt or other contaminant particles, potentially leading to infection of the patient. Tape also fails to limit catheter motion and, therefore, contributes to motion related complications like phlebitis, infiltration and catheter migration. Additionally, removal of taped dressings can itself cause undesired motion of the catheter upon the patient.

Taped dressings also require periodic changes. The frequent, often daily, removal and reapplication of adhesive tape to the skin of the patient can excoriate the skin in the area around the dressing. Such repeated applications of tape over the catheter or medical line can additionally lead to the buildup of adhesive residue on the outer surface of the catheter or medical line. This residue can result in contaminants adhering to the catheter itself, increasing the likelihood of infection of the insertion site. This residue can also make the catheter or medical line stickier and more difficult to handle for healthcare providers.

Accordingly, it would be desirable to provide a catheter securement device that is simple to use while providing reliable fixation of the catheter to the patient's skin.

SUMMARY OF THE INVENTION

The present invention relates systems, devices and methods for securing a catheter, tubing, medical line, or other medical device to a patient.

In some embodiments, a securement device for securing a medical device having a suture tab to a patient's body is provided. The device can include an adhesive pad having a first surface coated with an adhesive and a second surface; a tab receiving portion disposed on the second surface of the adhesive pad and along a side edge of the adhesive pad; and a downwardly extending post that extends from the top of the tab receiving portion towards the adhesive pad.

In some embodiments, the downwardly extending post is biased away from the side edge. In some embodiments, the downwardly extending post is biased at an angle between about 0 to 30 degrees from the vertical axis. In some embodiments, the downwardly extending post is configured to engage the suture tab.

In some embodiments, the adhesive pad comprises an opening under the tab receiving portion that is configured to receive the suture tab.

In some embodiments, the tab receiving portion is transparent.

In some embodiments, the securement device further includes a backing layer disposed over the adhesive, wherein the backing layer comprises a pull tab.

In some embodiments, the backing layer comprises a first portion disposed proximate the tab receiving portion and having a first pull tab, and a second portion disposed away from the tab receiving portion and having a second pull tab, wherein the first portion and the second portion are separably removable.

In some embodiments, the adhesive comprises a hydrocolloid adhesive. In some embodiments, the adhesive further includes an acrylic adhesive disposed on portions of the adhesive pad configured to be exposed to high stress.

In some embodiments, the adhesive pad has skin tone color. In some embodiments, the adhesive pad is transparent. In some embodiments, the tab receiving portion is shaped like a dome.

In some embodiments, the dome has a continuously smooth surface. In some embodiments, the dome has a flattened top portion.

In some embodiments, the tab receiving portion has a height that is less than or equal to the height of the medical device.

In some embodiments, a system for securing a medical device having a first suture tab to a patient's body is provided. The system can include a first engagement tab comprising an adhesive pad having a first surface coated with an adhesive and a second surface, a tab receiving portion disposed on the second surface of the adhesive pad and along a side edge of the adhesive pad, and a downwardly extending post that extends from the top of the tab receiving portion towards the adhesive pad, wherein the downwardly extending post is disposed through the first suture tab.

In some embodiments, the system further includes an overdressing covering at least a portion of the first engagement tab and the medical device.

In some embodiments, the system further includes a second engagement tab that is secured to a second suture tab on the medical device, wherein the second engagement tab is secured independently of the first engagement tab.

In some embodiments, the first engagement tab is pivotably engaged with the first suture tab and the second engagement tab is pivotably engaged with the second suture tab.

In some embodiments, a system for securing a medical device to a patient's body is provided. The system can include an adaptor having a first suture tab, wherein the adaptor is removably disposed over a portion of the medical device; and a first engagement tab comprising an adhesive pad having a first surface coated with an adhesive and a second surface, a tab receiving portion disposed on the second surface of the adhesive pad and along a side edge of the adhesive pad, and a downwardly extending post that extends from the top of the tab receiving portion towards the adhesive pad, wherein the downwardly extending post is disposed through the first suture tab.

In some embodiments, the system further includes an overdressing covering at least a portion of the first engagement tab, adaptor and the medical device.

In some embodiments, the system further includes a second engagement tab that is secured to a second suture tab on the adaptor, wherein the second engagement tab is secured independently of the first engagement tab.

In some embodiments, the adaptor comprises a channel for receiving the portion of the medical device. In some embodiments, the channel comprises a deformable liner. In some embodiments, the deformable liner is elastic and reversibly deformable. In some embodiments, the deformable liner is made of foam.

In some embodiments, a method of securing a medical device having a first suture tab to a patient's body is provided. The method can include providing a first engagement tab comprising an adhesive pad having a first surface coated with an adhesive and a second surface, a tab receiving portion disposed on the second surface of the adhesive pad and along a side edge of the adhesive pad, and a downwardly extending post that extends from the top of the tab receiving portion towards the adhesive pad; disposing the downwardly extending post through the first suture tab; and adhering the adhesive pad to the patient's body.

In some embodiments, the system further includes disposing an overdressing over at least a portion of the first engagement tab and medical device.

In some embodiments, the system further includes providing a second engagement tab and securing the second engagement tab to a second suture tab on the medical device, wherein the second engagement tab is secured independently of the first engagement tab.

In some embodiments, the system further includes removing a first portion of a backing layer disposed over the adhesive, wherein the first portion of the backing layer covers a portion of the adhesive proximate the tab receiving portion.

In some embodiments, the system further includes positioning the first engagement tab on the patient's body after the first portion of the backing layer is removed.

In some embodiments, the system further includes removing a second portion of the backing layer after the first engagement tab is positioned on the patient's body.

In some embodiments, a securement device for securing a medical device having a suture tab to a patient's body is provided. The device can include an adhesive pad having a first surface coated with an adhesive and a second surface; a base disposed on the second surface; an upwardly extending post that extends from the base and away from the adhesive pad, wherein the post is configured to engage the suture tab; and a cover that is slidably attached to the base portion and configured to have a closed configuration that covers the post and an open configuration that exposes the post.

In some embodiments, the cover is reversibly secured to the slot by a locking mechanism.

In some embodiments, the base has a slot and the cover has a rail which is slidably disposed in the slot.

In some embodiments, the locking mechanism generates a tactile indicator when the cover is moved between the closed configuration and open configuration. In some embodiments, the locking mechanism generates an audible indicator when the cover is moved between the closed configuration and open configuration. In some embodiments, the locking mechanism comprises a rounded protrusion disposed within the slot and a complementary rounded indentation disposed on the rail. In some embodiments, the locking mechanism comprises a rounded protrusion disposed on the rail and a complementary rounded indentation disposed within the slot.

In some embodiments, the device further includes a backing layer disposed over the adhesive, wherein the backing layer comprises a pull tab. In some embodiments, the backing layer comprises a first portion disposed proximate the base and having a first pull tab, and a second portion disposed away from the base and having a second pull tab, wherein the first portion and the second portion are separably removable.

In some embodiments, a system for securing a medical device to a patient's body is provided. The system can include an adaptor having a first suture tab, wherein the adaptor is removably disposed over a portion of the medical device; and a first securement device comprising an adhesive pad having a first surface coated with an adhesive and a second surface, a base disposed on the second surface, an upwardly extending post that extends from the base and away from the adhesive pad, and a cover that is slidably attached to the base portion and configured to have a closed configuration that covers the post and an open configuration that exposes the post, wherein the post is disposed through the first suture tab.

In some embodiments, the system further includes an overdressing covering at least a portion of the first securement device, adaptor and the medical device.

In some embodiments, the system further includes a second securement device that is secured to a second suture tab on the adaptor, wherein the second securement device is secured independently of the first securement device.

In some embodiments, the adaptor comprises a channel for receiving the portion of the medical device. In some embodiments, the channel comprises a deformable liner. In some embodiments, the deformable liner is elastic and reversibly deformable. In some embodiments, the deformable liner is made of foam.

In some embodiments, a method of securing a medical device having a first suture tab to a patient's body is provided. The method can include providing a first securement device comprising an adhesive pad having a first surface coated with an adhesive and a second surface, a base disposed on the second surface, an upwardly extending post that extends from the base and away from the adhesive pad, and a cover that is slidably attached to the base portion and configured to have a closed configuration that covers the post and an open configuration that exposes the post; disposing the post through the first suture tab; sliding the cover to the closed configuration; and adhering the adhesive pad to the patient's body.

In some embodiments, the method further includes disposing an overdressing over at least a portion of the first securement device and medical device.

In some embodiments, the method further includes providing a second securement device and securing the second securement device to a second suture tab on the medical device, wherein the second securement device is secured independently of the first securement device.

In some embodiments, a securement device for securing a medical device to a patient's body is provided. The device can include an adhesive pad having a first surface coated with an adhesive and a second surface; and a vacuum formed blister pack disposed on the second surface and shaped to conform to a portion of the medical device.

In some embodiments, the vacuum formed blister pack is molded to the portion of the medical device.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 6-10 illustrate embodiments of various adaptors that provide suture tabs to other medical devices.

FIGS. 12A-12E illustrate various embodiments of a securement device having a balloon.

FIGS. 13A-13F illustrate an embodiment of the securement device having a butterfly wrap configuration.

FIGS. 14A-14D illustrate an embodiment of the securement device using a gel pad.

FIGS. 26A-26D illustrate an embodiment of a securement device formed from a wire loop.

FIGS. 27A-27E illustrate an embodiment of a securement device having a sheath and hooks.

FIGS. 28A-28E illustrate an embodiment of a securement device having a snap-on feature and an expandable anchor.

FIGS. 31A-31C illustrate an embodiment of a securement device having anchors configured for subdermal penetration.

DETAILED DESCRIPTION

Figure 1:
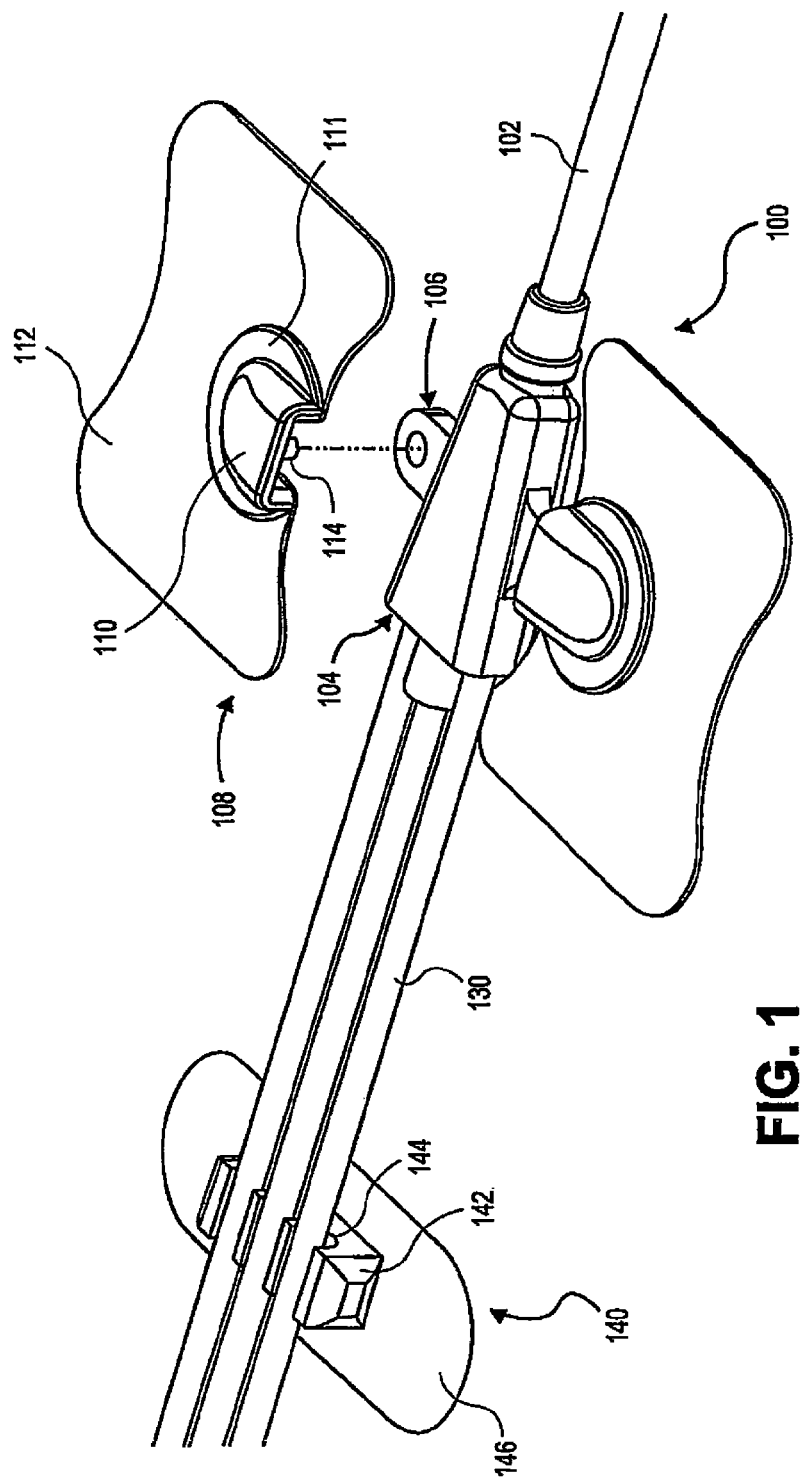
FIG. 1 is a perspective view of one embodiment of a modular catheter securement device.
Figure 2:
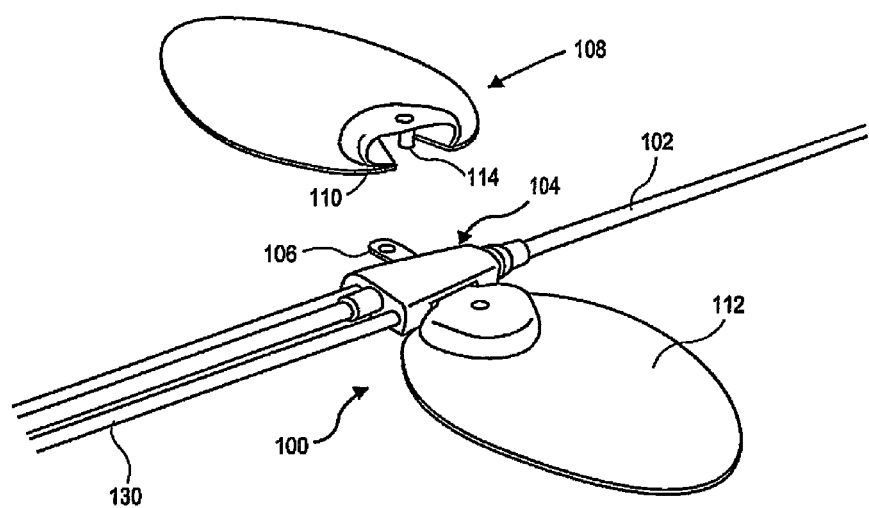
FIG. 2 is a perspective view of another embodiment of a modular catheter securement device.

FIGS. 1 and 2 illustrate an embodiment of a modular catheter securement system and/or device 100 that can be used to secure a catheter 102, tube or medical line having a catheter hub 104 with suture tabs 106 to a patient's skin. The securement device 100 includes independent and modular engagement tabs 108 that are configured to engage the suture tabs 106 and thereby secure the catheter hub 106 to the patient's skin. For a typical catheter with two suture tabs 106, the securement device 100 includes two engagement tabs 108. In general, the securement device 100 has an equal number of engagement tabs 108 as there are suture tabs 106. Since the engagement tabs 108 are independent and modular, more or fewer engagement tabs 108 can be used as needed.

Figure 3:
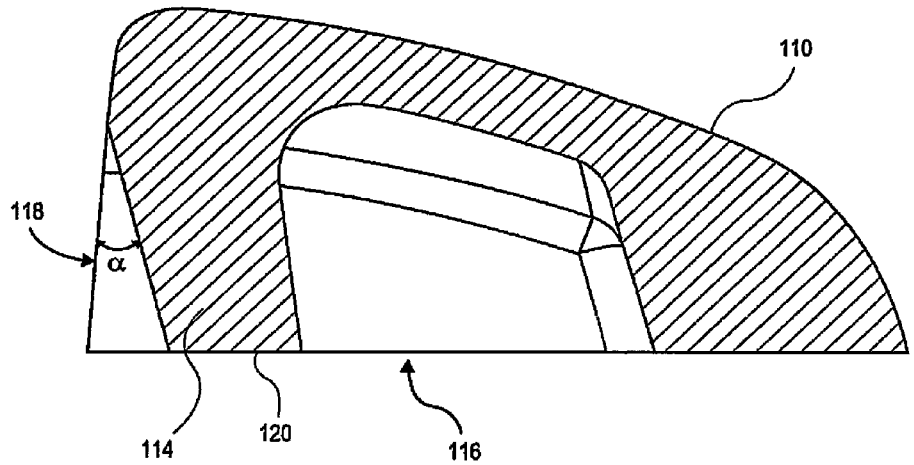
FIG. 3 is a cross-sectional view of an embodiment of an engagement tab of a modular catheter securement device.

The engagement tab 108 has a tab receiving portion 110 that is attached to an adhesive pad 112. The tab receiving portion 110 can have a cavity and an opening along the side facing the catheter hub 104 and along the bottom of the engagement tab 108 for receiving the suture tab 106. The tab receiving portion 110 can include a post 114 sized and shaped for engaging and passing through the hole in the suture tab 106. The tab receiving portion 110 can also have a base portion 111 that can be attached to the adhesive pad 112 and that provides stability to the tab receiving portion 110. As shown in FIG. 3, the post 114 can be made integral with the tab receiving portion 110 and can extend downwards from the top of the tab receiving portion 110 towards the bottom opening 116 of the tab receiving portion 110. The post 114 can be biased away from side opening 118 of the tab receiving portion 110, such that the distal end 120 of the post 114 is biased away from the suture tab 106 when the tab receiving portion 110 is engaged with the suture tab 106. The biased post 114 aids in preventing or reducing the likelihood of accidental disengagement of the tab receiving portion 110 from the suture tab 106 when the catheter 102 or catheter hub 104 is pushed downwards into the patient's skin. As the catheter 102 or catheter hub 104 is pushed downwards, the biased post 114 can exert an outwards and/or upwards force on the suture tab 106 that provides resistance to further downwards movement of the catheter 102 or catheter hub 104, thereby preventing and/or resisting accidental disengagement of the tab receiving portion 110 from the suture tab 106. In some embodiments, the post 114 can be angled between about 0 to 30 degrees, 0 to 25 degrees, 0 to 20 degrees, or 0 to 15 degrees from the vertical axis. In some embodiments, the post 114 is angled at least about 1, 2, 3, 4, 5, 10, 15, 20, 25, or 30 degrees from the vertical axis. In some embodiments, the post 114 can be angled less than about 5, 10, 15, 20, 25, or 30 degrees from the vertical axis. About or approximately as used herein can mean within 10%, 20%, or 30%, for example. In some embodiments, the post 114 can be tapered such that the distal end of the post 114 has a smaller diameter than the proximal portion of the post 114. In some embodiments, the post 114 is not tapered and has a constant diameter. In some embodiments, the distal end of the post 114 can include a barb, ball, or other retaining mechanism to improve retention of the post within the hole of the suture tab.

In some embodiments, the tab receiving portion 110 can be made of a flexible or semi-rigid material that can bend or flex in response to applied stress. The added flexibility enables the engagement portion 108 to absorb force exerted on the engagement portion 108, thereby reducing the force exerted on the catheter 102 and/or catheter hub 104 which reduces the risk of accidental dislodgement of the catheter 102 from the patient.

In some embodiments, the catheter 102 can include a plurality of lines 130 that can be secured to the patient with a line management device 140. The line management device 140 can comprise a body portion 142 with one or more channels 144 that can be disposed parallel to one another. The channels 144 are sized and shaped to receive the lines 130. The body portion 142 can be disposed on a adhesive pad 146 with features similar to that described herein.

As illustrated in FIG. 4, the adhesive pad 112 can include a peelable backing layer 122 to cover the adhesive on the adhesive pad 112. The backing layer 122 can have a pull tab 124 for removing the backing layer 122 from the adhesive pad 112 and thereby exposing the adhesive on the adhesive pad 112. In some embodiments, the backing layer 122 can be divided into multiple pieces, each with a separate tab 124 to facilitate peeling. For example, the backing layer 122 can have a first portion that covers the area around the tab receiving portion 110 and a second portion away from the tab receiving portion 110. Having two portions allows only a relatively small portion of the adhesive to be exposed while positioning the securement device on the patient, which may allow easier repositioning of the securement device. In other embodiments, the backing layer 122 can be formed of a single piece with a single tab 124 to facilitate peeling. The backing layer 122 can be removed before the adhesive pad 112 is pressed into contact with the patient's skin. In some embodiments, the backing layer 122 can be removed prior to inserting the post 114 through the hole in the suture tab 106. In other embodiments, the backing layer 122 can be removed after inserting the post 114 through the hole in the suture tab 106.

In some embodiments, the adhesive pads 112 can use a combination of an acrylic adhesive for the high stress points and a hydrocolloid adhesive for long term securement and comfort. In some embodiments, the adhesive pads 112 can use either the acrylic adhesive or the hydrocolloid adhesive. The backing layer 122 can be made from paper, plastic or any other suitable material that can be peeled from the adhesive. In some embodiments, a two or more securement devices 100 can be disposed on a single backing layer 122 that can be perforated or scored between the adhesive pads 122 of the securement devices 100 to allow the securement devices 100 to be held together during packaging and easy separation of the securement devices 100 from each other before use. The adhesive pad 112 substrate can be a skin tone fabric or a clear material that allows for the skin color to show through in order to minimize the visual impact of the device on the patient who may have to endure the catheter for many days. The adhesive pad 112 can be made of a flexible material so that it can conform to that geometry of the patient's body.

One unique feature of this design is that the securement device 100 comes in modular parts, such as the modular engagement tabs 108 that are each comprised of a tab receiving portion 110 on an adhesive pad 112. The engagement tab 108 is attached to each suture tab 106 on each side of the catheter hub 104 and adhered to the patient's skin. Because the engagement tabs 108 are separate and modular, the securement device can accommodate catheter hubs 104 of any width that uses suture tabs 106. This enables a universal fit for many catheter styles or brands.

Attaching the engagement tab 108 to the suture tab 106 on the catheter 102 is a simple maneuver that can be accomplished by simply engaging the post 114 of the engagement tab 108 into the hole of the suture tab 106 from the top down. This requires very little manipulation of the indwelling catheter 102 which is a priority of users. Since the modular engagement tabs 108 are independent, each engagement tab 108 can be optimally positioned sequentially according to the patient anatomy. This lends flexibility of placement which is another important feature for users. In addition, in some embodiments, the fit of the post 114 within the hole of the suture tab 106 can leave some room for the post 114 to pivot within the hole, which can further enhance the ability of the modular securement system to conform to the variable geometry of the patient's body. This can be accomplished, for example, by making the post 114 have a smaller diameter than the hole of the suture tab 106. The ability of the engagement tabs 108 to pivot on the suture tab 106 allows the engagement tabs 106 and catheter hub 104 or other device to each lie within different planes if needed, which aids the system in conforming to the patient's body. The adhesive pads 112 of each engagement tab 108 can be trimmed to any shape if needed. Once both engagement tabs 108 are in place, the catheter 102 is held extremely well by the adhesive pads 112. The shape and placement of adhesive provides resistance to lateral and upwards pulling of the catheter 102 or tubing, thereby ensuring proper securement of the catheter 102 to the patient.

In some embodiments, the engagement tab 108 can be dome shaped with curved surfaces, as illustrated in FIGS. 1 and 2. The dome in FIG. 2 has a continuously smooth surface while the dome in FIG. 1 has a non continuous smooth surface with a flattened top portion. In some embodiments, a dome with a continuously smooth surface can be more easily covered with an overdressing such that pockets of air trapped between the overdressing and dome are reduced. The engagement tab 108 can be made of a transparent material, such as a transparent plastic, that allows the user to visualize the post 114 through the walls of the dome forming the tab receiving portion 110. The post 114 can be made opaque so that it is easier to visualize. For example, the post can be coated or made from an opaque material. The discrete shape and size of the dome permits full visualization of the catheter hub and skin entry point. The engagement tab 108 can have a low profile which enables smooth placement of overdressings, such as Tegaderm™, over the catheter 102, catheter hub 104, and/or securement devices 100. For example, the engagement tab 108 can have a height that is less than or equal to the height of the catheter 102 and/or the catheter hub 104. This results in a securement device 100 with optional overdressing that is no higher than the catheter 102 or catheter hub 104 itself with no obtrusive bumps, housings, catch points and the like for maximum patient comfort while reducing the likelihood of accidentally snagging and dislodging or removing the catheter 102, catheter hub 104 and/or securement device 100.

Figure 4A:
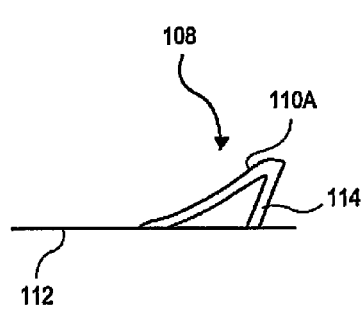
FIGS. 4A-5B illustrate other embodiments of the engagement tab.
Figure 4B:
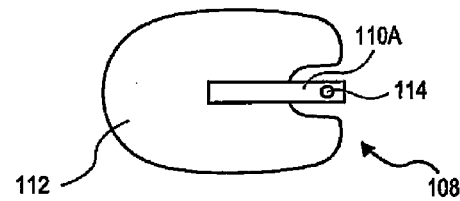
Figure 4C:
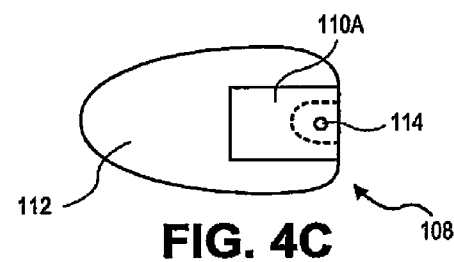

In some embodiments, as illustrated in FIGS. 4A-4C, the engagement tab 108 can have an alternative tab receiving portion 111. Rather than a dome shaped tab receiving portion 110 as shown in FIGS. 1-3, the engagement tab 108 can have a tab receiving portion 111 formed from an angled strip of material with a post 114 extending downwards from the distal end of the strip. As above, the post 114 can be biased inwards and away from the distal end of the strip. The strip can be straight or curved. In curved embodiments, the curve can be convex, concave, or a combination of convex and concave curves. As above, the strip-like engagement tab 108 can be flexible or semi-rigid, which enables to engagement tab 108 absorb force exerted on the engagement tab 108, which reduces the force exerted on the catheter 102 and/or catheter hub 104. One difference between the strip-like engagement tab and the dome-like engagement tab is that the post 114 is shielded by the dome and accessible in the strip embodiment. In some embodiments, it can be easier to manipulate the post 114 without detaching the adhesive pad 112 from the skin in the strip embodiment in the event that the post 114 becomes dislodged and needs to be repositioned through the suture tab 106. In some embodiments, a dome or enclosure can be placed over the strip-like engagement tab 108 to form a hybrid embodiment.

Figure 5A:
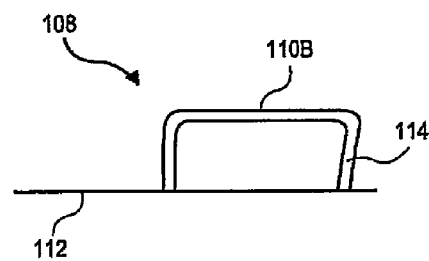
Figure 5B:
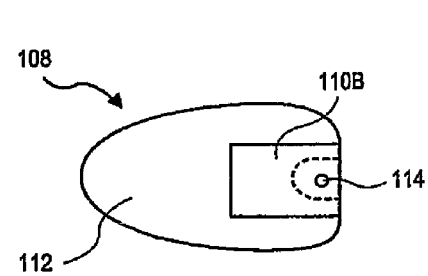

An alternative embodiment of the engagement tab is illustrated in FIGS. 5A and 5B. The engagement tab 110B is can be form an enclosure like the dome embodiment, except that the shape of the enclosure can be rectangular or square. The engagement tab 110B can have the other features described for the dome embodiment, such as having a biased post 114 and be made from a transparent material. In some embodiments, the enclosure can be partially rectangular or square and partially curved.

In some embodiments, the catheter and/or catheter hub may not have suture tabs to which the securement device can be attached. In this situation, adaptors can be used to provide suture tabs to the catheter. Various adaptors can be used to fit over catheters, luer connectors, standard catheter hubs, custom catheter hubs, and other catheter related parts near the insertion point. The combination of the modular securement device with an adaptor allows the securement device to be used in a large variety of catheters For example, FIG. 6 illustrates one embodiment of an adaptor 200 that can be fastened to a luer connector, catheter, or other generally tubular catheter related part. The adaptor 200 can have an adaptor body 202 and a channel 204 disposed through or within the adaptor body 202 for receiving the luer connector, catheter, or other generally tubular catheter related part. The adaptor body 202 can have or rest on a base 206 that is configured to be placed on the patient's skin. The base 206 can include suture tabs 208 that extend transversely away from the channel 204 to which engagement tabs 108 can be fastened to as described above.

In some embodiments, the channel 204 or the longitudinal axis of the channel 204 can be angled downwards with respect to the base 206 or plane defining the base 206. For example, the channel 204 can be angled downwards between about 0 to 5, 0 to 10, 0 to 15, 0 to 20, 0 to 25, 0 to 30 degrees, 0 to 35, 0 to 40, or 0 to 45 degrees with respect to the base. The angled channel 204 allows the distal end of the catheter to be pointed towards the skin, thereby allowing the user to more easily control the angle of insertion of a needle or the catheter into the patient's body. Control of the angle of insertion along with the distance of insertion is important in preventing or reducing the forces that the indwelling device exerts on the patient's tissue, which can help reduce damage to the tissue.

Figure 8:
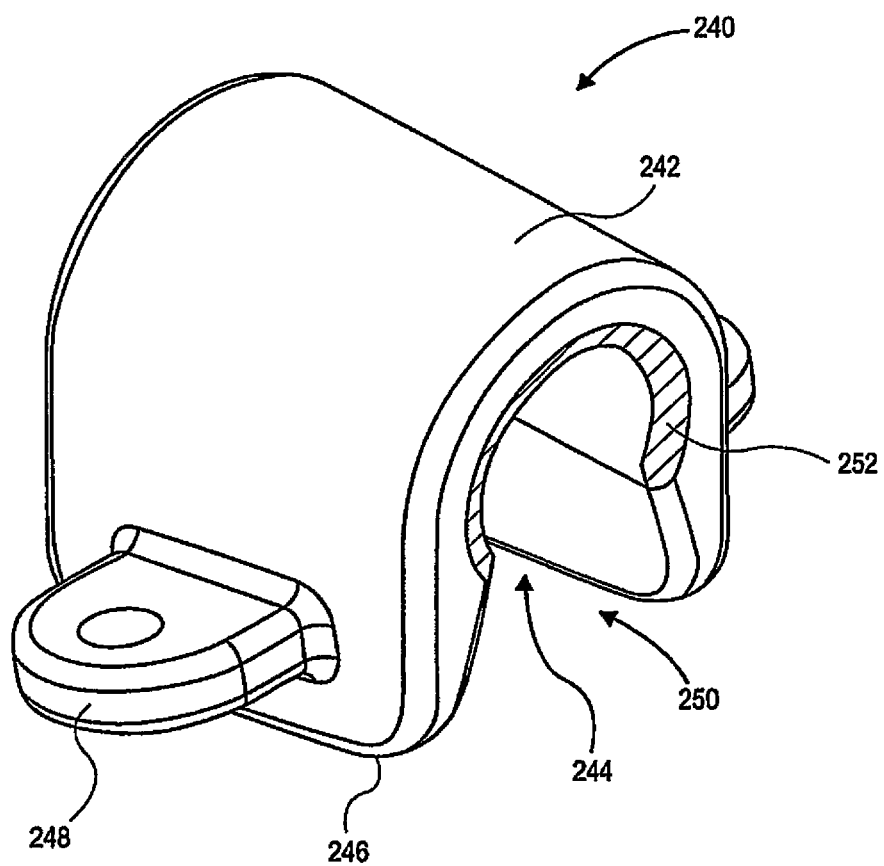

In some embodiments, the base 206 can have an access slot 210 that provides access to the channel 204. The access slot 210 can run parallel to the channel 204. In some embodiments, the access slot 210 can have a width that is less than the diameter of the channel 204, which allows the channel 204 to securely retain the inserted device without the device inadvertently falling out. In some embodiments, the access slot 210 tapers such that the width of the access slot 210 adjacent to the channel 204 is narrower than the diameter of the channel 204, while the diameter of the access slot 210 gradually increases in width as it moves away from the channel 204, as illustrated in FIG. 8, for example. In some embodiments, the adaptor body 202 can have a plurality of alignment slots 212 that are oriented transversely to the axis of the channel 204. These alignment slots 212 can function as alignment features by restraining a tab on the luer connector, catheter, or other generally tubular catheter related part, to restrain the axial movement of the catheter within the adaptor 200. In some embodiments, the adaptor body 204 does not have alignment slots 212.

In some embodiments, the channel 204 can be coated or covered with a liner that can provide a gripping surface to secure the inserted device. The liner can be soft, elastic, spongy, resilient and/or reversibly deformable to conform to the inserted device and to allow the adaptor 200 to secure a wider variety of inserted devices. In some embodiments, the liner can be made of a foam or sponge material. In some embodiments, the liner can be expandable and filled with a liquid, gel and/or a gas. The liner can be included in any of the adaptor embodiments described herein.

FIG. 7 illustrates another embodiment of an adaptor 220 having an adaptor body 222 that encloses a channel 224. The base 226 can be integral with the adaptor body 222. Suture tabs 228 can be provided that extend from the base 226, and to which engagement tabs 108 can be secured. In some embodiments, including other embodiments described herein, the suture tabs 228 can be offset from the base 226. In the illustrated embodiment, the adaptor body 222 can be made of two sections 230, 231 that together define the channel 224 and can be connect together by a hinge 232 that allows the two sections 230, 231 to be separated, thereby exposing the channel 224 and allowing a device to be inserted into the channel 224. A locking mechanism 234, such as a latch for example, can be used to reversibly secure the two sections 230, 231 together. As described above, the channel 224 can be angled with respect to the base 226. An alignment feature 236 on the top surface of the adaptor body 222 can indicate to the user which direction in which to insert the device into the channel. The alignment feature 236 can also be included in the other adaptor embodiments described herein.

FIG. 8 illustrates another embodiment of an adaptor 240. The adaptor 240 has an adaptor body 242 that defines a channel 244 for receiving an inserted device as described herein. As described herein, the channel 244 can be angled with respect to the base 246. The body 242 can have a base 246 and suture tabs 248 that are offset from the base 246. The offset can be between about 0 to 2, 0 to 4, 0 to 6, 0 to 8, or 0 to 10 mm. An access slot 250 can be provided on the bottom of the adaptor body 242 to provide access to the channel 244. As described above, the access slot 250 can have a taper such that it is narrower than the diameter of the channel 244 at a point adjacent to the channel 244, but progressively widens as the access slot 250 moves away from the channel 244. This configuration provides a larger target zone for insertion of the inserted device into the channel 244, and also acts to funnel the inserted device to the channel 244, thereby facilitating insertion of the inserted device into the channel 244. The channel 244 can have a liner 252 for gripping the inserted device, as further described herein in other embodiments. For example, the liner 252 can be soft, elastic, and/or deformable, which allows the liner 252 to conform to inserted devices of a variety of shapes and sizes.

Figure 9:
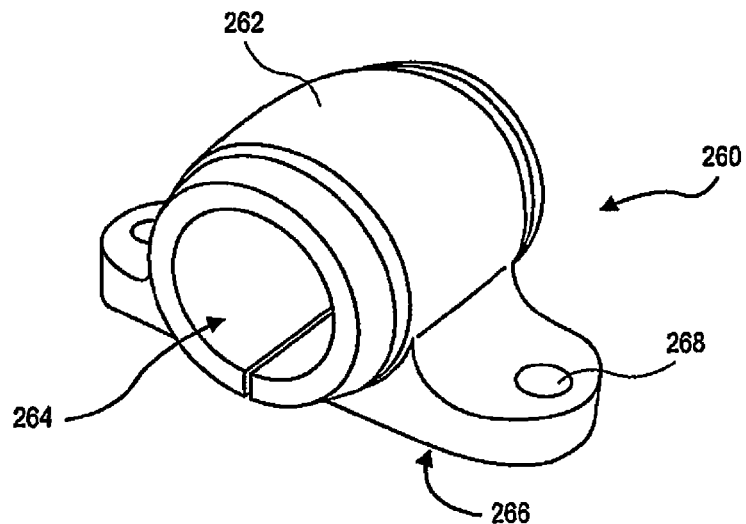

FIG. 9 illustrates another embodiment of an adaptor 260 that can be used to provide suture tabs to a catheter, luer adapter, and the like. The adaptor 260 can include an adaptor body 262 that encircles or partially encircles a channel 264. The adaptor body 262 can have a base 266, which can be integral to the adaptor body 262. The suture tabs 268 can extend from the base 266 and also be integral to the base 266. A slot 270 can be formed in the base 266 to provide access to the channel 264 and to divide the base 266 into two separable parts. The body 262 can be made of a flexible material, such as rubber or another flexible elastomeric polymer, such that the slot 270 can be widened by deforming the body 262. For example, force can be applied downwards on the top portion of the body 262 while an upwards force can be applied to the suture tabs 268 in order to widen the slot 270 so that the adaptor 260 can be placed over the inserted device. In some embodiments, the slot 270 can be narrow or closed in the unstressed configuration such that the channel 264 substantially encloses an entire circumference. In other embodiments, the slot 270 can be wider, such as in the embodiments disclosed above, so that the channel 264 is configured to encircle only a portion of the inserted device, which is typically at least 50% of the circumference of the inserted device. As above, the channel 264 can be angled with respect to the base, and the channel 264 can include a liner.

Figure 10:
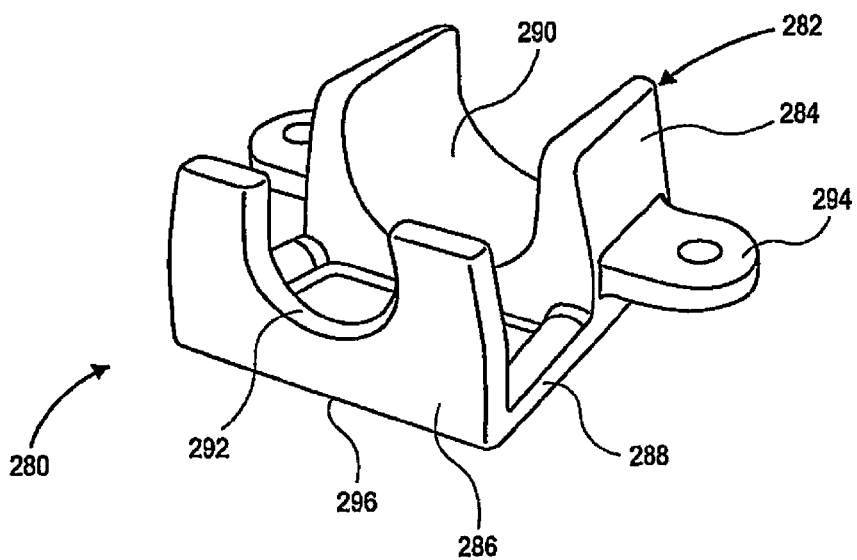

FIG. 10 illustrates another embodiment of an adaptor 280 that can be used to secure a specialty catheter or hub, such as neural block catheter, for example. The adaptor 280 can include a adaptor body 282 having a first portion 284, a second portion 286 and a third portion 288 disposed between the first portion 284 and the second portion 286. The first portion 284 can include an open channel 290 formed at the top of the first portion 284, such that the inserted device can be inserted into the channel 290 from above by pushing the inserted device downwards into the channel 290. The second portion 286 also includes a second open channel 292 formed at the top of the second portion 286. The second channel 292 may have the same or may have a different cross-sectional profile than the first channel 290. In some embodiments, both the first channel 290 and the second channel 292 have arcuate, semi-circular cross-sectional profiles. In some embodiments, the length of the first channel 290 is greater than the length of the second channel 292. In some embodiments, the length of the first channel 290 is the same as or greater than the length of the second channel 292. The third portion 288 can be a flat depression with a surface that lies below the lowest point of the first channel 290 and the second channel 292. In some embodiments, the suture tabs 294 can extend outwards from the first portion 286 and can be offset from the base 296 of the adaptor body 282. As described above, the first channel 290 and/or the second channel 292 can be angled with respect to the base, and a liner can be added to either channel.

Figure 11C:
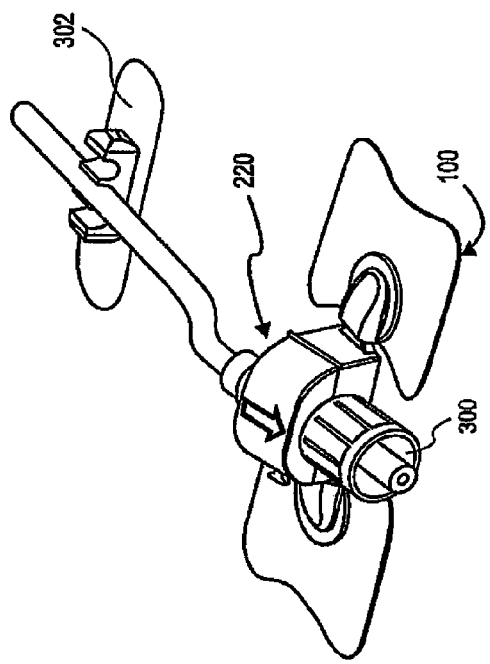
FIGS. 11A-11E illustrate the securement of catheters with various embodiments of the adaptors and engagement tabs.
Figure 11A:
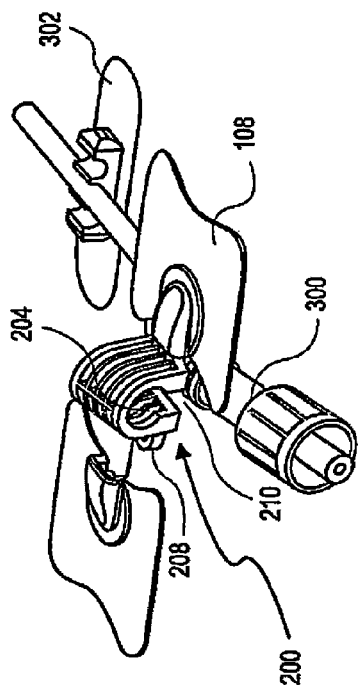
Figure 11B:
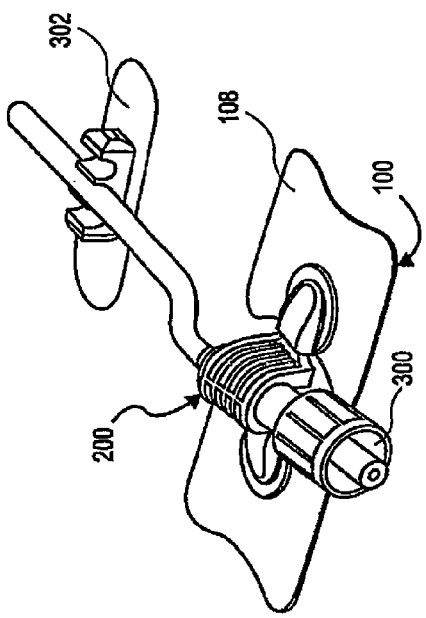

FIGS. 11A-11E illustrate the attachment of the adaptors described herein to luer adaptors or specialty hubs. For example, FIGS. 11A and 11B illustrate the attachment of the adaptor 200 described in FIG. 6 with a luer adaptor and the attachment of engagement tabs 108 to the suture tabs 208 provided by the adaptor 200, thereby securing the catheter in place. In practice, the adaptor 200 can first be placed over the luer adaptor 300 by, for example, snapping the luer adaptor 300 through the access slot 210 and into the channel 204 in order to provide suture tabs 208 to the luer adaptor 300. A securement device 100 can then be attached to the suture tabs 208 as described above. A line management device 302 can be used to secure the lines of the catheter.

FIG. 11C illustrates the attachment of the adaptor 220 described in FIG. 7 to a luer adaptor 300. As described above, the adaptor 220 can be opened into two pieces and then locked over the luer adaptor 300 to provide suture tabs 228 to the luer adaptor. A securement device 100 can then be attached to the suture tabs 228 as described above. A line management device 302 can also be used to secure the lines of the catheter.

Figure 11D:
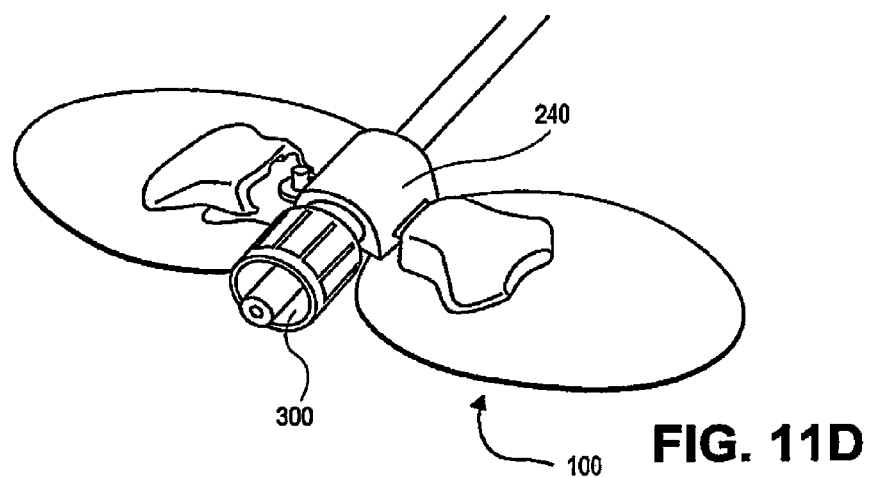
Figure 11E:
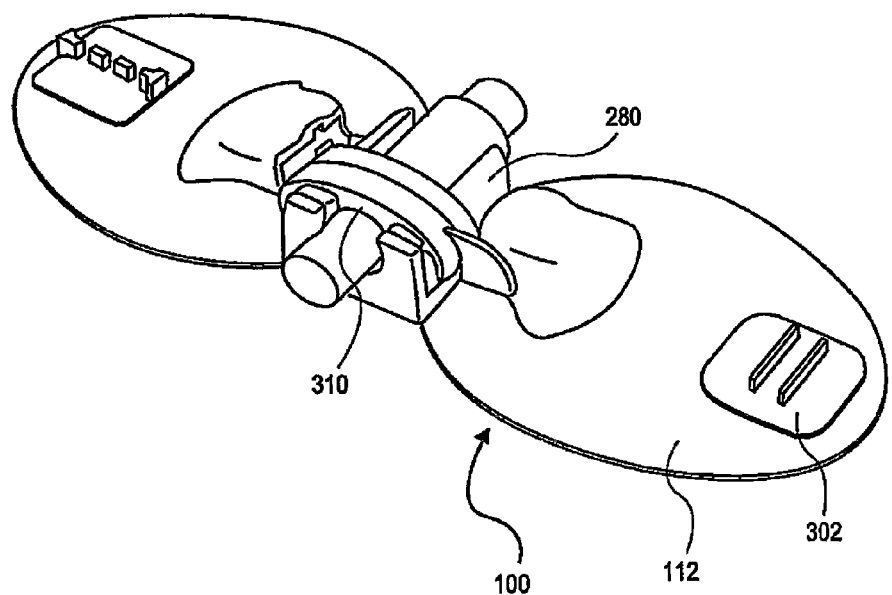

Similarly, FIGS. 11D-11E illustrate the attachment of the adaptors described in FIGS. 8-10 to either a luer adaptor 300 or a specialty hub 310 to provide suture tabs to the luer adaptor 300 or specialty hub 310. One the suture tabs are provided, a securement device 100 can be attached to the suture tabs as described above. A line management device 302 can also be used to secure the lines of the catheter. In some embodiments, the line management device 302 can be attached to top portion of the adhesive pad 112.

Alternative Securement Devices

FIGS. 12A-12E illustrate another embodiment of a securement device 1200. The securement device 1200 includes an adhesive pad 1202 and an inflatable tube 1204 disposed on or integral to the adhesive pad 1202. The inflatable tube 1204 can have an inflation port 1206 that can be used to inflate the inflatable tube 1204 with a gas or liquid. In some embodiments as illustrated in FIGS. 12D and 12E, the inflatable tube 1204 further includes a longitudinal split 1208 that allows the inflatable tube 1204 to partially unfurl, which can make insertion or removal of the catheter 1210 through the inflatable tube 1204 easier. To secure the catheter 1210, the catheter 1210 can be inserted through the inflatable tube 1204 and then the inflatable tube 1204 can be inflated to compress the catheter 1210 within the inflatable tube 1204. As the inflatable tube 1204 is inflated, the diameter of the inflatable tube 1204 decreases until contact is made with the catheter 1210.

FIGS. 13A-13F illustrate another embodiment of a securement device 1300. The securement device 1300 includes an adhesive pad 1302 and an adhesive wrap 1304 that is attached to the adhesive pad 1302. The adhesives on the adhesive pad 1302 and the adhesive wrap 1304 can be disposed on the nonadjacent surfaces of each so that the adhesive pad 1302 can be attached to the patient's skin and the adhesive wrap 1304 can be wrapped over a catheter 1306 or other device placed on top of the adhesive wrap 1304. The adhesive wrap 1304 can be flexible so that it can be easily wrapped over and around the catheter 1306. The adhesive wrap 1304 can be either permanently or reversibly attached to the adhesive pad 1302. Reversible attachment can be accomplished by using adhesives, hook and loop fasteners, latches, clips and the like. Generally, the middle portion 1308 of the adhesive wrap 1304 is attached to the adhesive pad 1302 such that the adhesive wrap 1304 has two wings 1310 than can be used to wrap around the catheter. Both the adhesive wrap 1304 and the adhesive pad 1302 can be covered by one or more backing layers which can be peeled off to expose the adhesive.

FIGS. 14A-14D illustrate another embodiment of a securement device 1400. The securement device 1400 includes an adhesive pad 1402 and a gel pad 1404 disposed on the adhesive pad 1402. An adhesive film 1406 can be disposed over the gel pad 1404 to secure a catheter 1408 or other device that has been placed on the gel pad 1404. The gel pad 1404 can provide compression around the catheter 1408 and can further be coated or impregnated with an antimicrobial agent. The adhesive film 1406 can be transparent and can be removably adhered over the gel pad 1404 and catheter 1408.

Figure 15A:
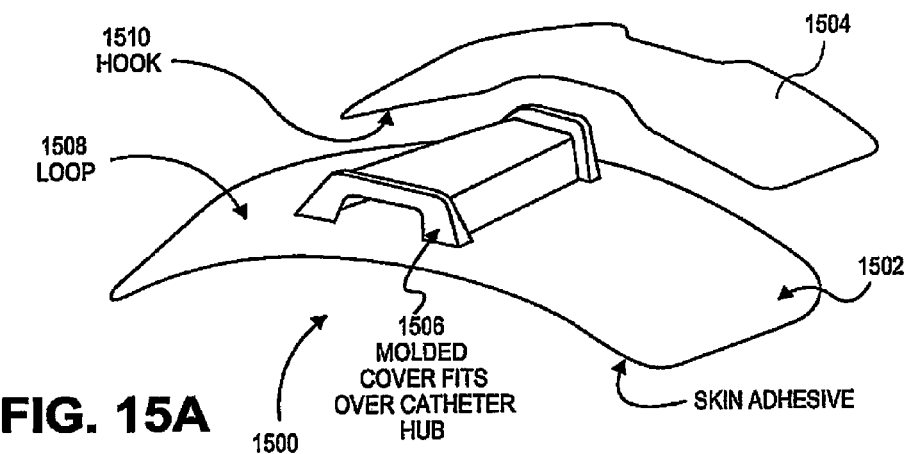
FIGS. 15A-15G illustrate various embodiments of securement devices using a hook and loop fastener.
Figure 15B:
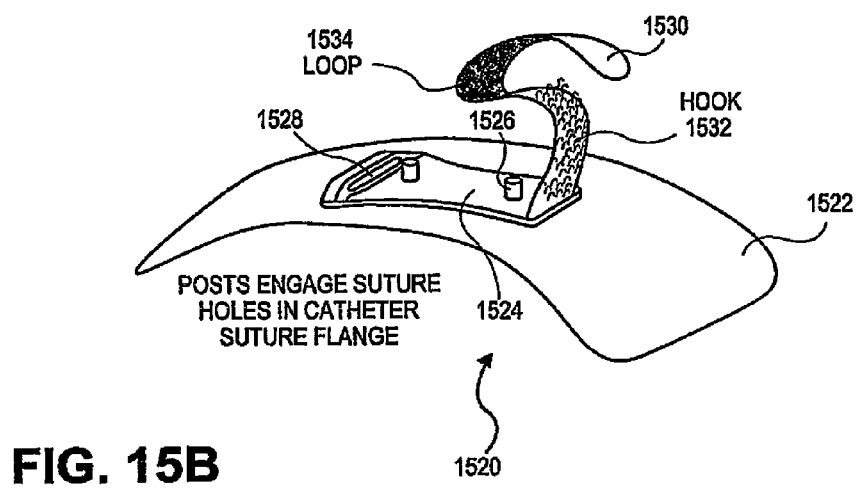
Figure 15C:
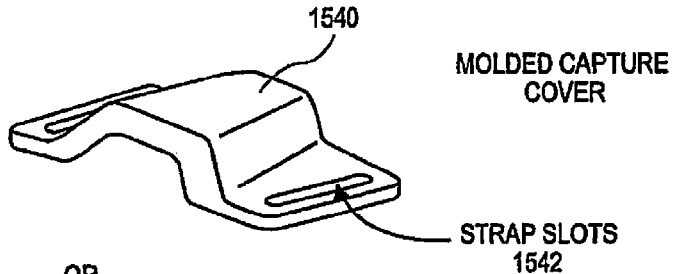
Figure 15D:
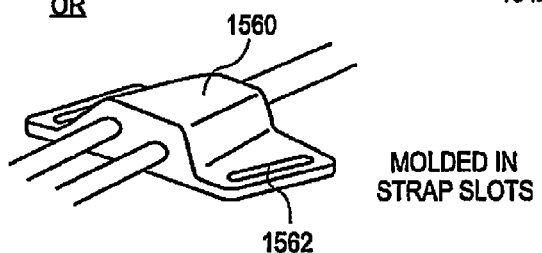
Figure 15E:
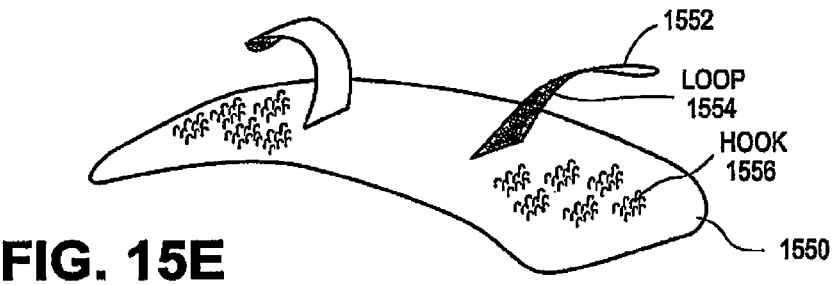
Figure 15F:
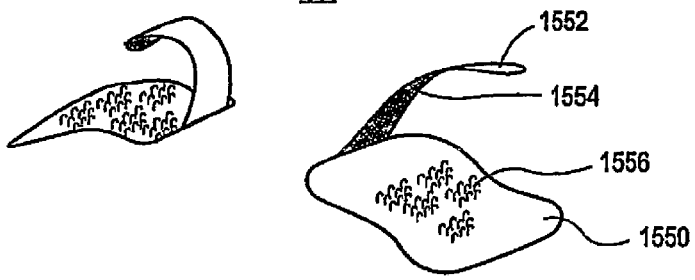
Figure 15G:
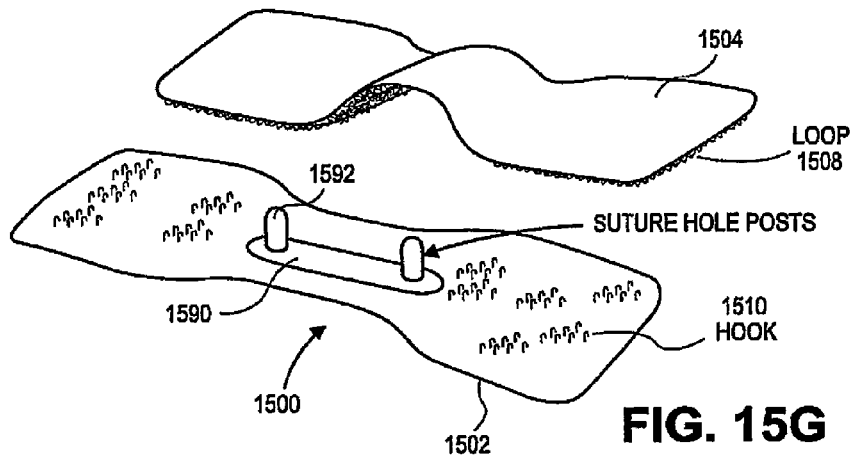

FIGS. 15A-15G illustrate additional embodiments of securement devices involving a hook and loop fastener. For example, FIG. 15A illustrates a securement device 1500 having an adhesive pad 1502 with an adhesive on one side to bind to skin and loops 1508 or hooks on the other side. A flexible covering 1504 has hooks 1510 or loops complementary to the adhesive pad 1502 disposed on one side of the flexible covering 1504. A molded cover 1506 can optionally be used to cover the catheter or catheter hub or other device that is placed on the adhesive pad 1502. The molded cover 1506 can be shaped and sized to conform to the catheter, catheter hub or other device. After the device is placed on the adhesive pad 1502, the flexible covering 1504 is fastened to the adhesive pad 1502 over the device using the hook and loop fastener. FIG. 15G illustrates another embodiment of a securement device that is similar to the embodiment described in FIG. 15A. The difference is that the molded cover 1506 shown in FIG. 15A is replaced with a base 1590 have two posts 1592 that can engage the holes in the suture tabs of a catheter hub.

FIG. 15B illustrates another embodiment of a securement device 1520. The securement device 1520 can have an adhesive pad 1522 and a base 1524 disposed on the adhesive pad 1522. The base 1524 can optionally have posts 1526 sized and spaced to fit through the suture tabs on a catheter hub. One side of the base 1526 can have a slot 1528 for receiving a strap 1530 that is attached to the other side of the base 1526. A portion of one side of the strap 1530 can be covered in hooks 1532 and another portion of the same side of the strap can be covered in loops 1534. To secure the catheter hub, the suture holes of the catheter hub are disposed over the posts 1526, if present, and the strap 1530 is passed over the catheter hub and through the slot 1528. The strap 1530 is then tightened and can be looped back on itself such that the hooks and loops on the strap 1530 are engaged to secure the strap 1530.

FIGS. 15C and 15D illustrate a molded capture cover 1540 with strap slots 1542 and a catheter hub 1560 with molded in strap slots 1562, respectively, that can be used with the adhesive pads illustrated in FIGS. 15E and 15F. FIG. 15E illustrates an adhesive pad 1550 having two attached straps 1552. The straps 1552 can be spaced apart to match the separation of the strap slots in the molded capture cover or catheter hub. One side of each strap 1552 can be covered with a loop 1554 or hook material while an area of the adhesive pad 1550 adjacent or proximate the strap 1552 is covered with a complementary hook 1556 or loop material to secure the strap 1552. The straps 1552 are designed to be folded outwards towards the ends of the adhesive pad 1550. FIG. 15F illustrates a two piece embodiment of the adhesive pad illustrated in FIG. 15E where the middle portion between the straps has been removed to form two adhesive pads 1550, each with a single strap 1552 located on one edge of the adhesive pad 1550. To secure the molded capture cover 1540 or catheter hub 1560 to the adhesive pad 1550, the strap 1552 is passed through the strap slot 1542, 1562 and then looped back on itself so that the hook and loop material engage each other. The two piece adhesive pads 1550 can be used with a wide variety of molded capture covers and molded catheter hubs of different sizes as long as each have strap slots.

Figure 16:
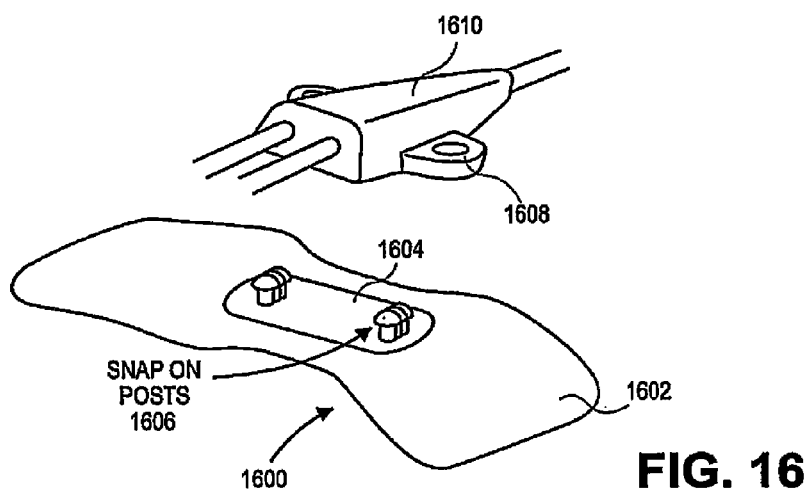
FIG. 16 illustrates an embodiment of a securement device using snap on posts.

FIG. 16 illustrates a securement device 1600 having an adhesive pad 1602, a base 1604 disposed on the adhesive pad 1602. The base 1604 can have a pair of snap-on posts 1606 that can snap into the holes on the suture tabs 1608 of a catheter hub 1610. The snap-on posts 1606 can be made by cutting a post in half and then separating the two halves by a small distance such that gap is formed between the two halves. The posts 1606 can have tapered end portions that are wider than the post stem, such that insertion of the posts 1606 into the holes forces the two halves of each post 1606 together until the tapered end portions pass through the hole, after which the post halves can once again separate. The width or diameter of the two tapered end portion halves when separated can be slightly larger than the hole diameter, and the width or diameter of the two tapered end portion halves when pushed together can be smaller than the hole diameter. This allows the tapered end portion to pass through the hole while providing a restraining effect after passing through the hole.

Figure 17:
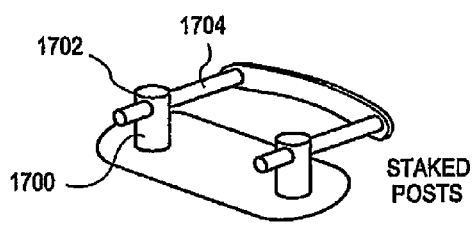
FIG. 17 illustrates an embodiment of a securement device using staked posts.

FIG. 17 illustrates an embodiment of a post 1700 having a hole 1702 oriented transversely to the post axis. The hole 1702 can be located proximate the free end of the post 1700. A pin 1704 or stake can be inserted through the hole 1702 in order to secure a suture tab that has been placed over the post 1700. The pins 1704 can be connected together or can be independent.

Figure 18:
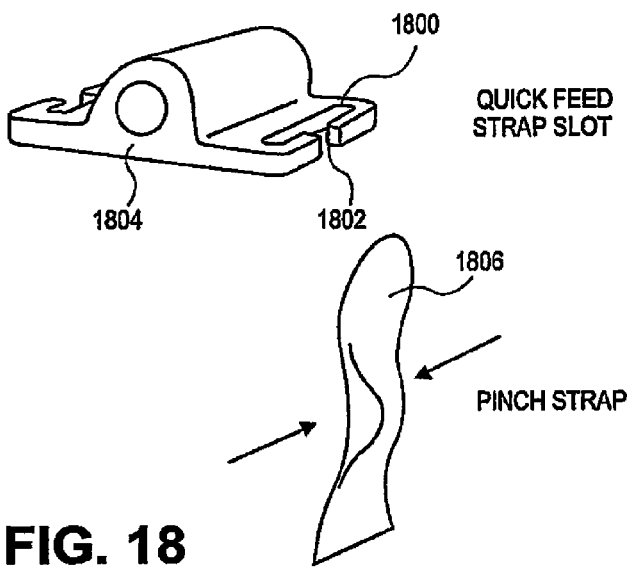
FIG. 18 illustrates an embodiment of a quick feed strap slot.

FIG. 18 illustrates an embodiment of a quick feed strap slot 1800. The quick feed strap slot 1800 has an opening 1802 that is narrower than the slot 1800 and in communication with the slot 1800 that provides access to the slot 1800 from the side of the hub 1804 or device. A strap 1806 can be pinched together to narrow the width of the strap 1806, which can be then passed through the opening 1802 and into the slot 1800.

Figure 19:
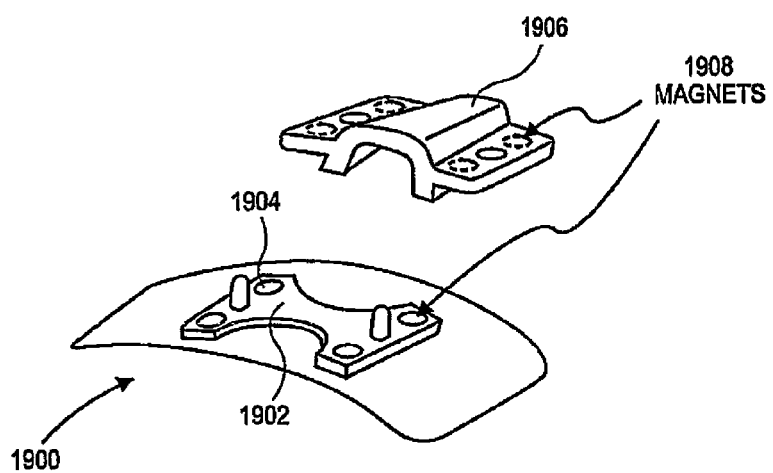
FIG. 19 illustrates an embodiment of a securement device using magnets.

FIG. 19 illustrates an embodiment of a securement device 1900 that uses a base 1902 with one or more magnets 1904 to secure a molded cover 1906 or molded hub with complementary magnets 1908. The attractive force between the complementary magnets located on the base and the molded cover secures the parts together.

Figure 20:
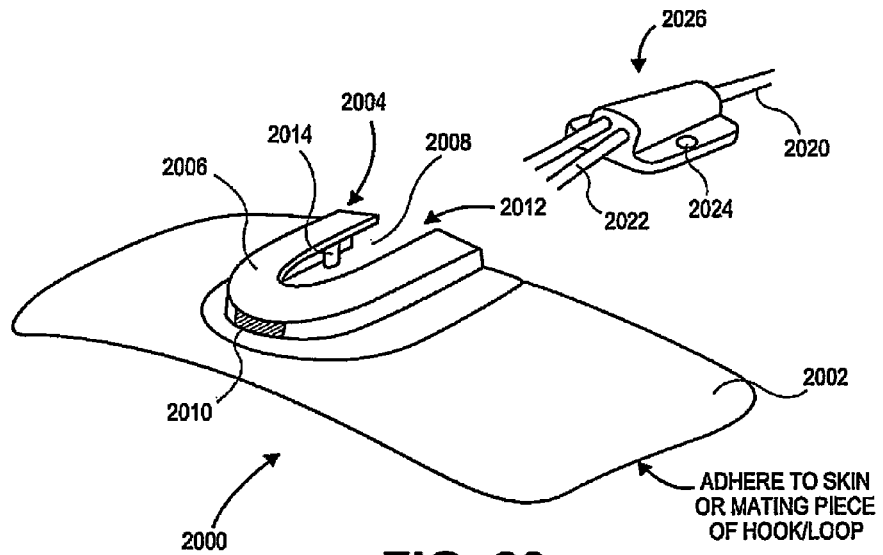
FIG. 20 illustrates another embodiment of a securement device using downwardly extending posts.

FIG. 20 illustrates another embodiment of a securement device 2000 that has an adhesive pad 2002 and slot retainer 2004 disposed on the adhesive pad 2002. The slot retainer 2004 can have a housing 2006 with a slot 2008 located on the top of the housing 2006. The slot retainer 2004 and two openings 2010, 2012 to pass the catheter 2020 and lines 2022. The housing 2006 can also have downward extending posts 2014 for engaging the holes 2024 suture tabs of the catheter hub 2026. The housing 2006 is designed to be placed over the catheter hub 2026 with the posts 2014 engaging the holes in the suture tabs. In some embodiments, a portion of the hub can extend through the slot 2008 in the housing 2006.

Figure 21:
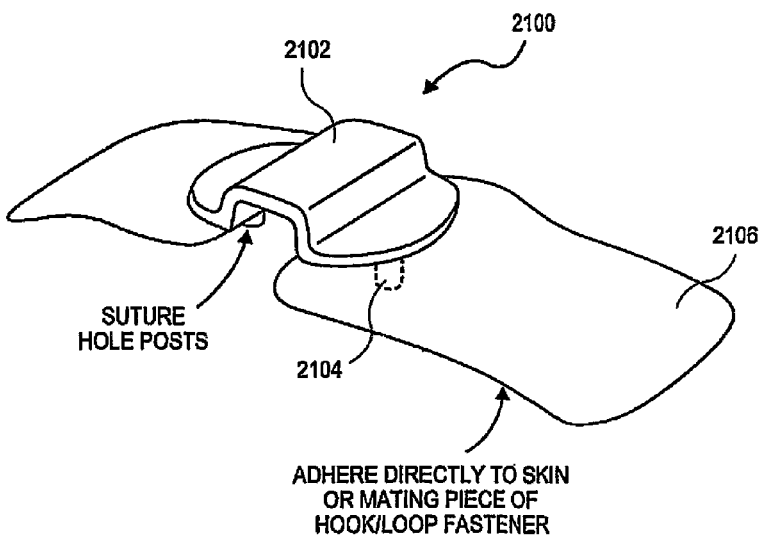
FIG. 21 illustrates yet another embodiment of a securement device using downwardly extending posts.

FIG. 21 illustrates another embodiment of a securement device 2100 with a molded cover 2102 having a pair of downwardly extending posts 2104 and two flexible wings 2106. If the wings 2106 are coated with an adhesive, the wings 2106 can be directly adhered to the patient's skin. If the wings 2106 are covered with a hook and loop fastener material, the wings 2106 can be fastened to an adhesive pad with complementary hook and loop fastener material. The posts 2104 can be inserted into the holes of suture tabs.

Figure 22A:
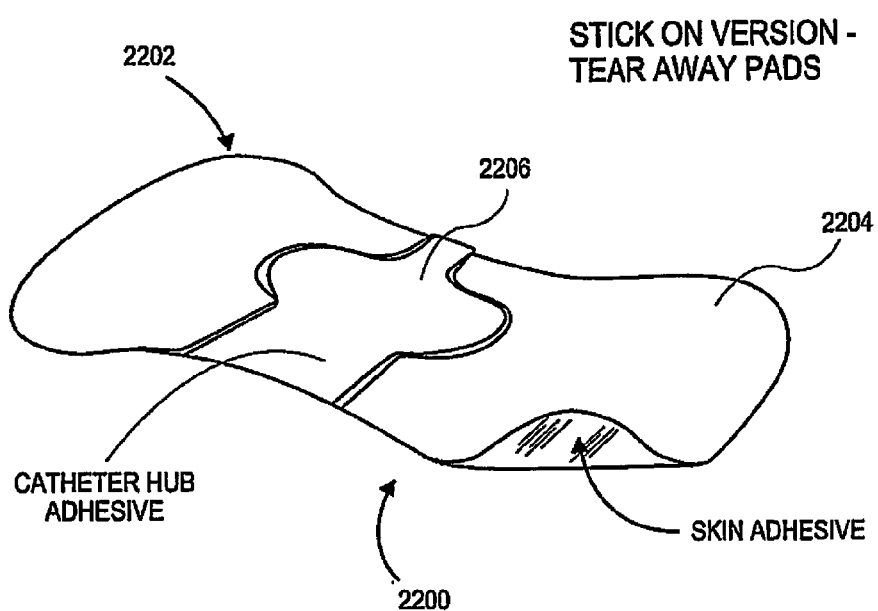
FIGS. 22A-22C illustrates an embodiment of a securement device using tear-away pads.
Figure 22B:
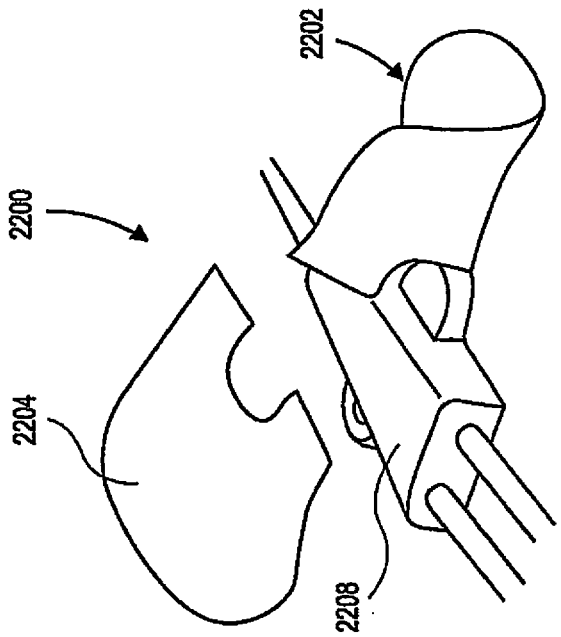
Figure 22C:
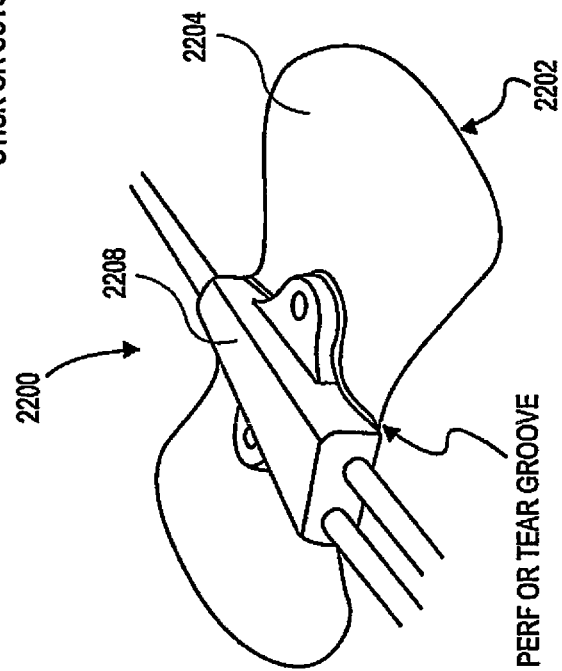

FIGS. 22A-22C illustrate another embodiment of a securement device 2200 having an adhesive pad 2202 with tearaway side portions 2204. The bottom surface of the adhesive pad 2202 can be coated with an adhesive. The central portion 2206 of the adhesive pad 2202 can also have an adhesive coating the top surface. The central portion 2206 can be sized and shaped to match a catheter hub 2208 or other device such that the catheter hub can be adhered to the central portion 2206. The side portions 2204 can be optionally torn away from the central portion 2206. The boundary line between the side portions 2204 and the central portion 2206 can be perforated or scored to facilitate separation of the side portions 2204.

Figure 23:
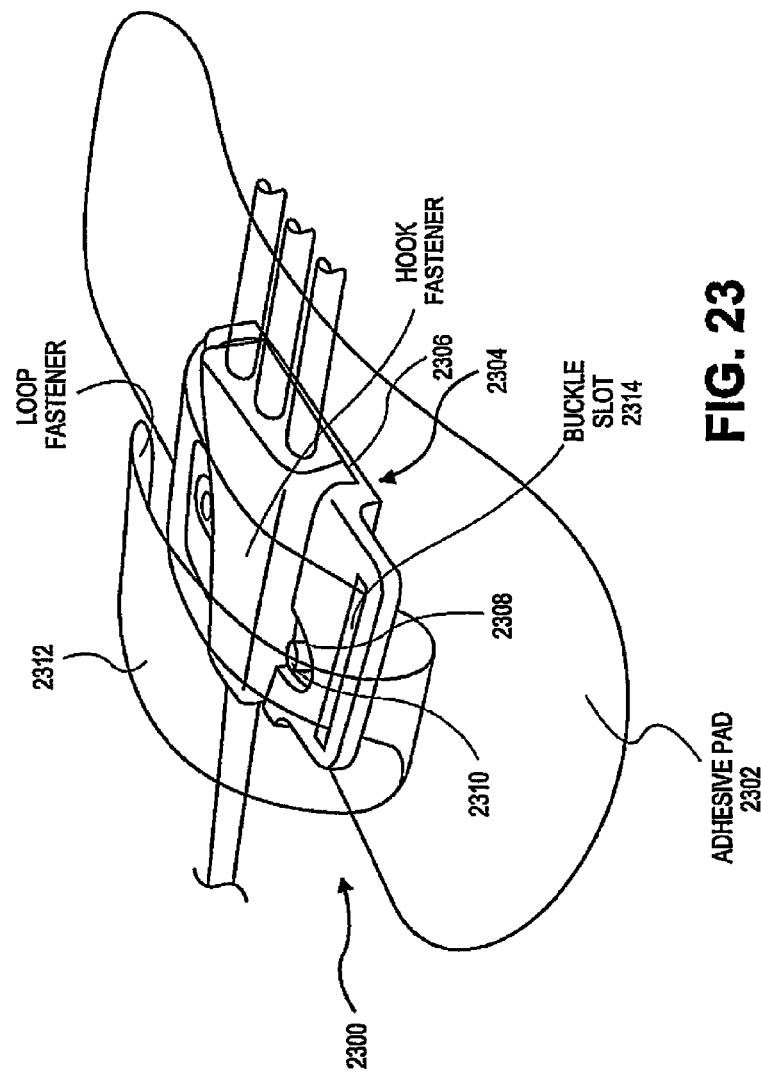
FIG. 23 illustrates an embodiment of a securement device using a strap and buckle over a nested hub to secure a catheter.

FIG. 23 illustrates another embodiment of a securement device 2300 having an adhesive pad 2302 and a nested hub 2304 secured to the adhesive pad 2302. The nested hub 2304 can have a receiving portion 2306 shaped to receive a catheter hub. The receiving portion 2306 can also have suture tab receiving portions 2308 for receiving the suture tabs on the catheter hub. The suture tab receiving portion 2308 can have a post 2310 for securing the suture tabs. The nested hub 2304 can have a strap 2312 attached to one side of the nested hub 2304 and a buckle slot 2314 located on the other side of the nested hub 2304. The strap 2312 can be used to secure a catheter hub placed in the nested hub 2304. To secure the catheter hub, the strap 2313 can be passed through the buckle slot 2314, tightened, and then fastened to itself using a fastener such as hook and loop fasteners.

Figure 24A:
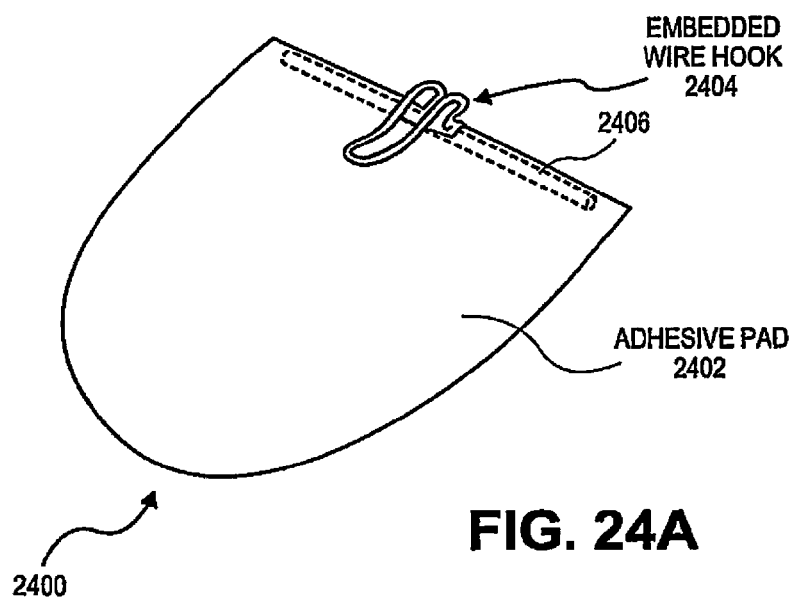
FIGS. 24A and 24B illustrate an embodiment of a securement device having wire hooks.
Figure 24B:
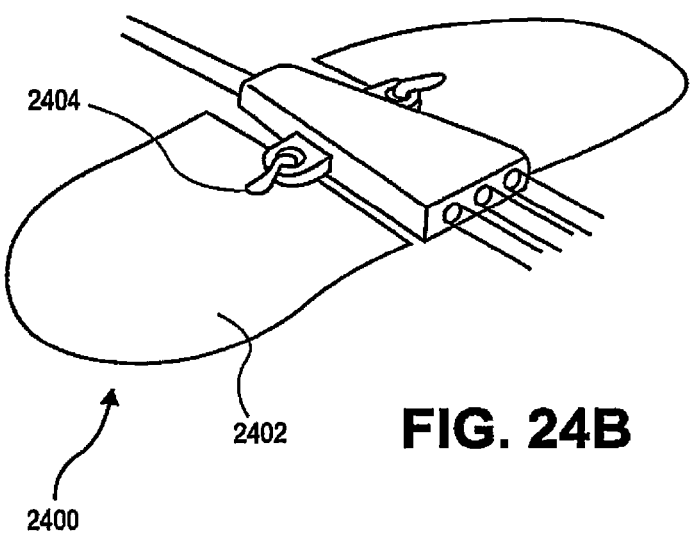

FIGS. 24A and 24B illustrate another embodiment of a securement device 2400. The securement device 2400 is formed from an adhesive pad 2402 that has an embedded hook 2404 that can pass through the hole in the suture tab and lock the suture tab in place. The hook 2404 can be made of a metal or plastic wire. The hook 2404 can be rotationally or pivotably attached to the adhesive pad 2402 and can be biased to a closed position. The hook 2404 can have an axle portion 2406 that can be rotatably attached to the adhesive pad 2402. For example, the axle portion 2406 can be threaded through the adhesive pad 2402 or can be disposed in a channel in the adhesive pad 2402. The channel can be formed by molding or by folding a portion of the adhesive pad over itself. The bias can be applied by a spring attached to the hook 2404. To pass the hook 2404 through the suture tab, the hook 2404 can be rotated so that it faces upwards and can be threaded through the hole in the suture tab. When the hook 2404 is released, the hook's 2404 natural bias to the closed position can automatically rotate the hook 2404 back to the closed position, thereby securing the suture tab. For securing a catheter hub having two suture tabs, two securement devices 2400 can be used as shown in FIG. 24B to secure the catheter hub to the patient.

Figure 25:
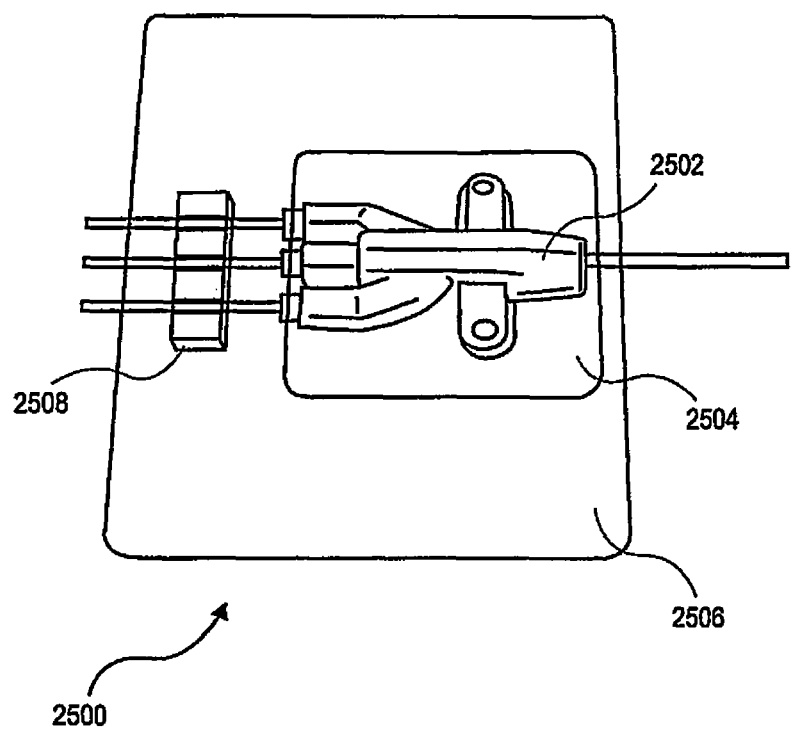
FIG. 25 illustrates an embodiment of a securement device made from a vacuum formed blister pack.

FIG. 25 illustrates another embodiment of a securement device 2500. The securement device 2500 includes a vacuum formed blister pack 2502 that can be formed to match the size and shape of any catheter hub or other portion of a catheter or medical device by using the catheter hub, catheter or medical device as a mold for the blister pack. The blister pack 2502 can have a base 2504 with an adhesive that allows the base 2504 to function as an adhesive pad. The base 2504 can be adhered directly to the patient's skin or adhered to an adhesive pad or overlay 2506 with an integrated tube or line management structure 2508. In some embodiments, the blister pack 2502 can be integrated into the adhesive pad with the line management structure.

FIGS. 26A-26D illustrate another embodiment of a securement device 2600. The securement device 2600 is formed from a coiled wire with a plurality of spiral loops 2602 and a penetrating tip 2604. The securement device 2600 can also have a handle 2606 to facilitate rotation of the securement device 2600 over the catheter. The securement device 2600 is placed over a catheter such that the catheter is disposed through the loops 2602 of the wire. Rotating the coils drives the penetrating tip 2604 in a corkscrewing action into the patient's skin, thereby securing the catheter to the patient's skin. The catheter can have grooves for guiding and holding the loops of the wire coil in place on the catheter. The coils can grip the catheter sufficiently to secure the catheter on the patient. In some embodiments, the diameter of the loops in an unstressed state is smaller than the diameter of the catheter in order for the loops to provide sufficient force against the catheter.

FIGS. 27A-27E illustrate another embodiment of a securement device 2700. The securement device 2700 is a catheter anchor formed by an anchor portion 2702 having one or more hooks 2704 extending from a collar portion 2706. For example, the anchor portion 2702 can have two hooks, three hooks, four hooks, or greater than four hooks. The collar portion 2706 fits over the catheter and can be secured or fastened to the catheter. In some embodiments, the collar portion 2706 can be snapped over the catheter. An anchor sheath 2708 can be disposed over the anchor portion 2702 to cover the hooks 2704 during catheter insertion. The hooks 2704 can be elastic or superelastic such that the hooks can be straightened out by the sheath in a covered low profile configuration. To deploy the hooks 2704, the sheath 2708 can be retracted from the anchor portion 2702 to expose the hooks 2704, which bend elastically back towards its deployed configuration with the tips of the hooks extending outwards and into the tissue, thereby anchoring the catheter. In some embodiments, the catheter securement device 2700 can be advanced over the catheter and partially into the patient's skin before the sheath 2708 is retracted to expose the hooks 2704. The remove the catheter, the sheath 2708 can be advanced back over the hooks 2704 to compress the hooks against the catheter, thereby allowing the catheter to be removed.

FIGS. 28A-28E illustrate another embodiment of a securement device 2800. The securement device 2800 can be made from a snap on sheath 2802 or tube that can snap onto a catheter to provide anchoring. The sheath 2802 can have a slit 2804 or gap that allows the sheath 2802 to be snapped onto the catheter. The securement device 2800 can have a radially expandable anchor portion 2806 that has a deployed configuration and a non-deployed configuration, where the anchor portion 2806 has a low profile in the non-deployed configuration, as shown in FIG. 28B, such as being in line with the rest of the sheath 2802. In the deployed configuration, the anchor portion 2806 can have a radially expanded profile with an increased diameter relative to the non-deployed configuration, as illustrated in FIG. 28C. In some embodiments, the anchor portion 2806 can be deployed by actuating the proximal portion 2808 of the sheath 2802, for example by retracting the proximal portion 2808, which retracts the distal portion 2810 of the sheath 2802 and compresses the anchor portion 2806. As the anchor portion 2806 is axially compressed, it expands radially outwards, thereby anchoring the catheter in the tissue. In some embodiments, the anchor portion 2806 can be deployed within the epidermis or dermis layer of the skin, or between the epidermis and dermis, or below the epidermis or dermis, such as subcutaneous deployment for example. In some embodiments, the anchor portion 2806 can be deployed within other tissues or cavities or lumens within the body. In some embodiments, the anchor portions 2806 can be stowed after deployment by, for example, advancing the proximal portion 2808 to advance the distal portion 2810 of the sheath 2802 and decompress the anchor portion 2806. As the anchor portion 2806 is axially decompressed, it retracts radially inwards until it no longer protrudes from the catheter or is flush with the catheter.

In some embodiments, as illustrated in FIG. 28D, the proximal portion 2808 can be provided with grip wing 2812 or other gripping features that facilitate the gripping, actuating, retracting and/or advancing of the proximal portion 2808 to deploy or stow the anchor portion 2806. In some embodiments, as illustrated in FIG. 28E, the sheath 2802 can have a inflation port 2814 that is in fluid communication of the anchor portion 2806 and that allows the anchor portion 2806 to be inflated and deflated to radially expand and retract the anchor portion 2806. The anchor portion 2806 can be inflatable such as a balloon, for example.

Figures 29A, 29B:
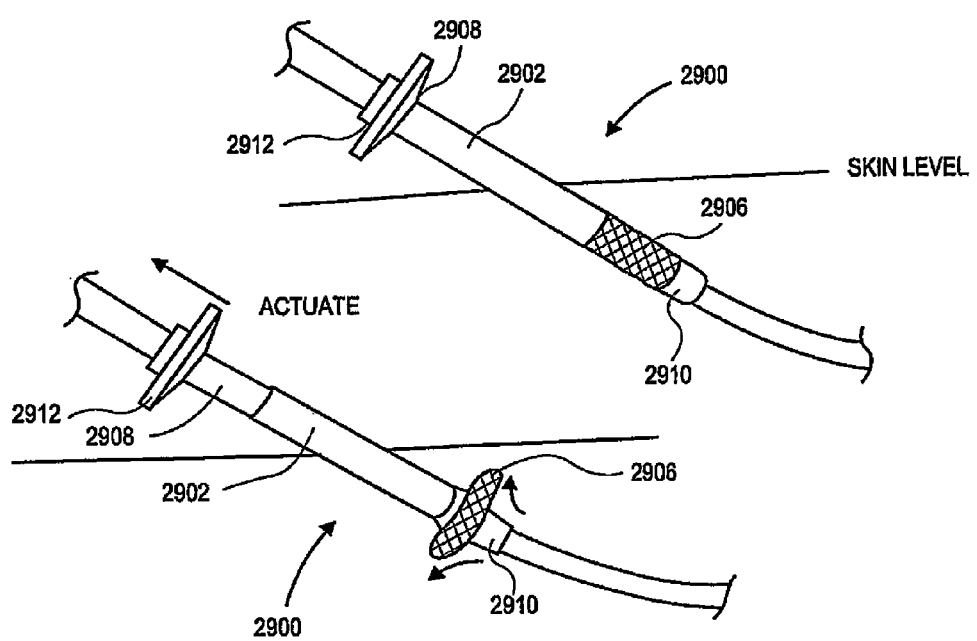
FIGS. 29A and 29B illustrate another embodiment of a securement device having an having an expandable anchor.

FIGS. 29A and 29B illustrate another embodiment of a securement device 2900 with an expanding anchor portion 2906 that is similar to the expanding anchor portion described above in FIGS. 28A-C. In some embodiments as illustrated in FIGS. 29A and 29B, the securement device 2900 can have a sheath 2902 that completely encircles the catheter 2902 and can be integrated with the catheter. In some embodiments, the sheath 2902 can have a longitudinal slit as described above to allow the securement device 2900 to be removably attached to the catheter. The sheath 2902 can have a radially expandable anchor portion 2906 that can be made of a mesh or woven material. In other embodiments, the anchor portion 2906 can be made of a membrane or sheet. As described above, the proximal portion 2908 of the sheath 2902 can be actuated, for example retracted proximally, which causes the distal portion 2910 of the sheath 2902 to also retract proximally to collapse and radially expand the anchor portion 2906. Also as described above, the proximal portion 2908 can be advanced distally to decompress the anchor portion 2906 to restore the anchor portion 2906 to its non-deployed state. The proximal portion 2908 can have a gripping portion 2912 that extends radially outwards and facilitates the gripping, actuating, retracting and/or advancing of the proximal portion 2908 to deploy or stow the anchor portion 2906.

Figure 30A:
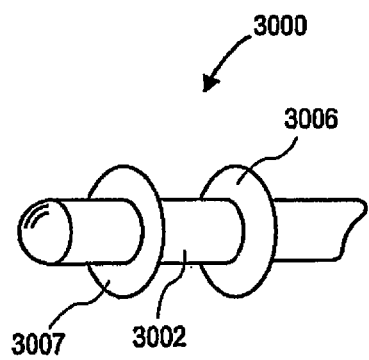
FIGS. 30A and 30B illustrate yet another embodiment of a securement device having an expandable anchor.
Figure 30B:
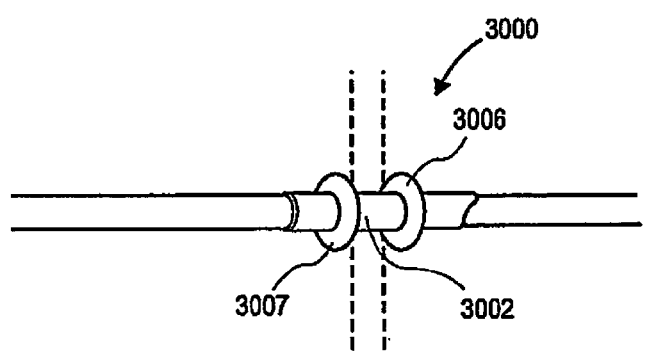

FIGS. 30A and 30B illustrate another embodiment of the securement device 3000 with two expandable anchor portions, a distal expandable anchor portion 3006 and a proximal expandable anchor portion 3007. The two anchor portions can be disposed on a sheath 3002 as described above and can be actuated in a similar manner to deploy the anchor portions. Providing a second anchor portion allows the anchor portions to sandwich the skin or other tissue layer between the anchors, thereby reducing the in and out movement of the catheter in the tissue. For example, the distal anchor portion 3006 can be deployed subcutaneously and the proximal anchor portion can be deployed 3007 against the outside surface of the skin. In some embodiments, the two anchors can be simultaneously deployed by a single actuation of the sheath, while in other embodiments, the two anchors can be independently deployed.

FIGS. 31A-31C illustrate another embodiment of a securement device 3100 that can be reversibly attached to a catheter. The securement device 3100 can have a base 3102 and a cover 3104. The base 3102 and cover 3104 can be attached together via a hinge 3105 or other mechanism that allows the cover 3104 to pivot with respect to the base 3102. The base 3102 and the cover 3104 can have a channel 3106 that is configured to receive the catheter and in conjunction with the base and cover forms a catheter shaft clamp area. The channel 3106 can have an opening in the proximal end of the base and cover assembly and an opening in the bottom portion of the base 3102 that allows the catheter to pass through the base and cover assembly and into the patient's skin. The cover 3104 can have one or more, for example two, anchor tangs 3108 that can be elongate and arcuate and have tissue penetrating tips. The base 3102 can have penetration guide channels 3110 that receive the anchor tangs 3108 and help guide and angle the anchor tangs 3108 into the skin. In some embodiments, the anchor tangs 3108 are configured to achieve subdermal or subcutaneous penetration. In some embodiments, the anchor tangs extend from the bottom surface of the cover 3104 such that cover is in the fully opened configuration, the tissue penetrating tips of the anchor tangs are disposed within the penetration guide channels 3110. The anchor tangs 3108 can be deployed to penetrate the patient's skin by closing the cover 3104 which drives the anchor tangs 3108 into the patient's skin. The anchor tangs 3108 can be driven into the skin at an angle such that the tissue penetrating tips are directed proximally. The guide channels 3110 can be oriented to slant proximally to facilitate entry of the anchor tangs 3108. When fully deployed, the anchor tangs 3108 can be positioned substantially longitudinally within or under the skin relative to the skin layer. In addition, the guide channels 3110 are located around or proximate the opening on the base 3102 where the catheter enters the skin. The location and orientation of the guide channels 3110 along with the shape and orientation of the anchor tangs 3108 allow the anchor tangs to enter the skin at the same location as the catheter entry so that no new entry site is created. Instead, the anchor tangs 3108 can enter alongside the catheter shaft. The cover 3104 can be secured to the base using a latching mechanism 3112 or other locking or fastening mechanism.

Figure 32A:
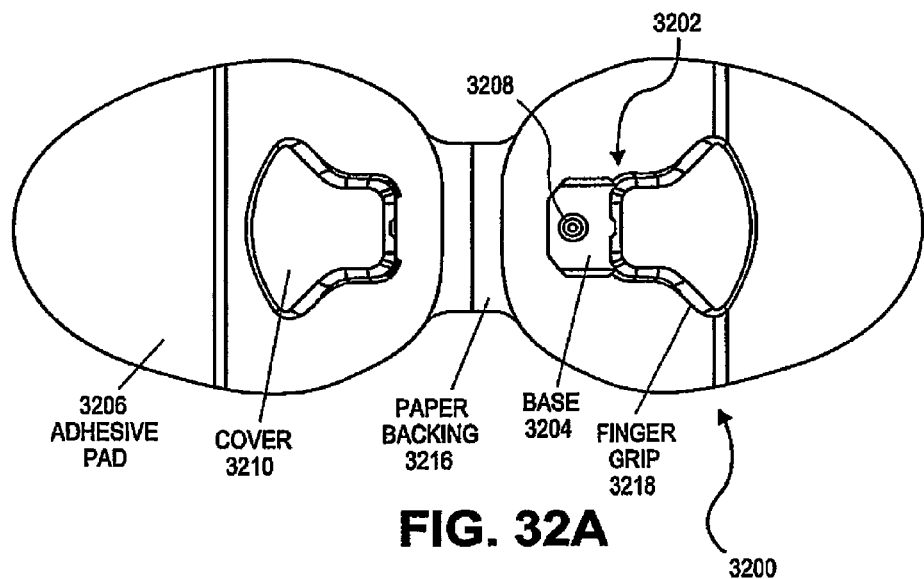
FIGS. 32A-32P illustrate an embodiment of a securement device having a slide-locking feature.
Figure 32B:
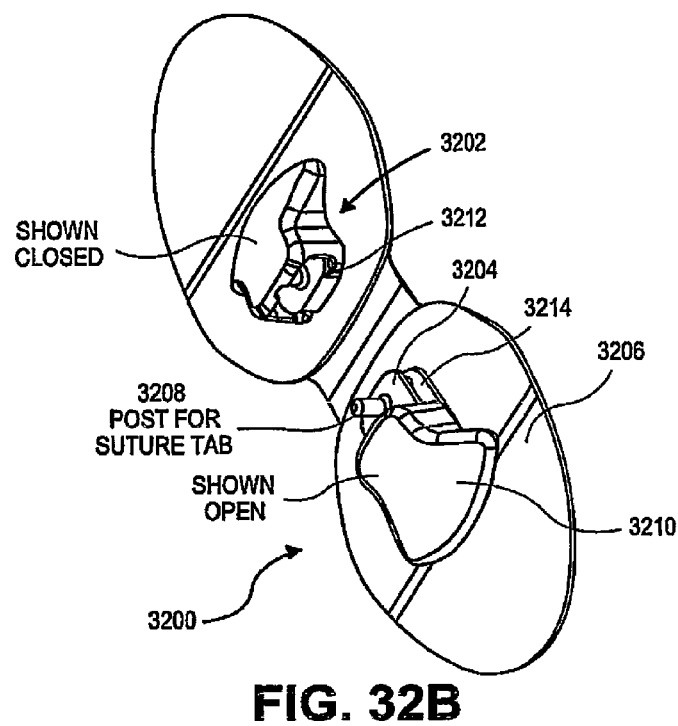
Figure 32C:
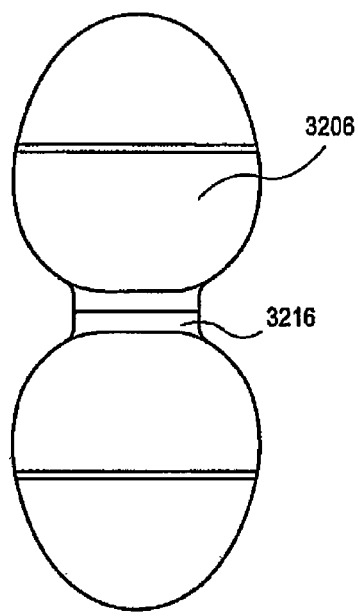
Figure 32D:
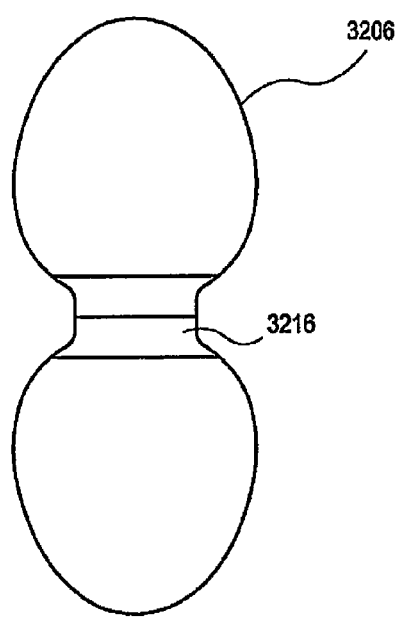
Figure 32L:
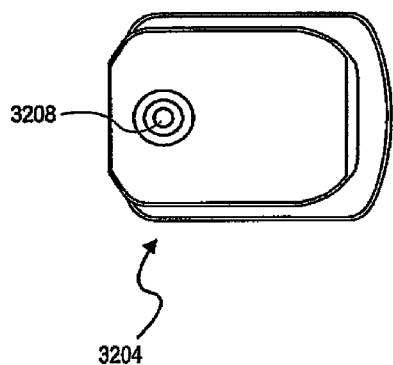
Figure 32M:
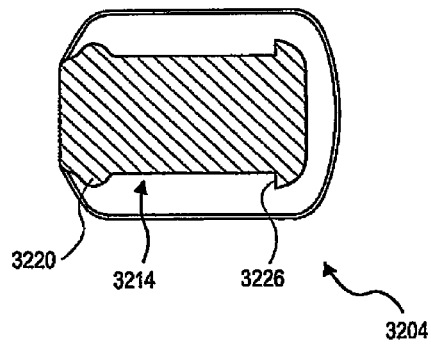
Figure 32N:
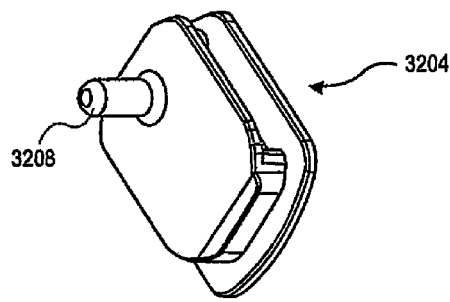
Figure 32O:
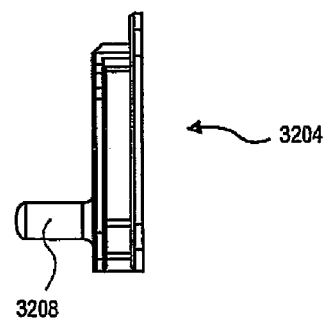
Figure 32P:
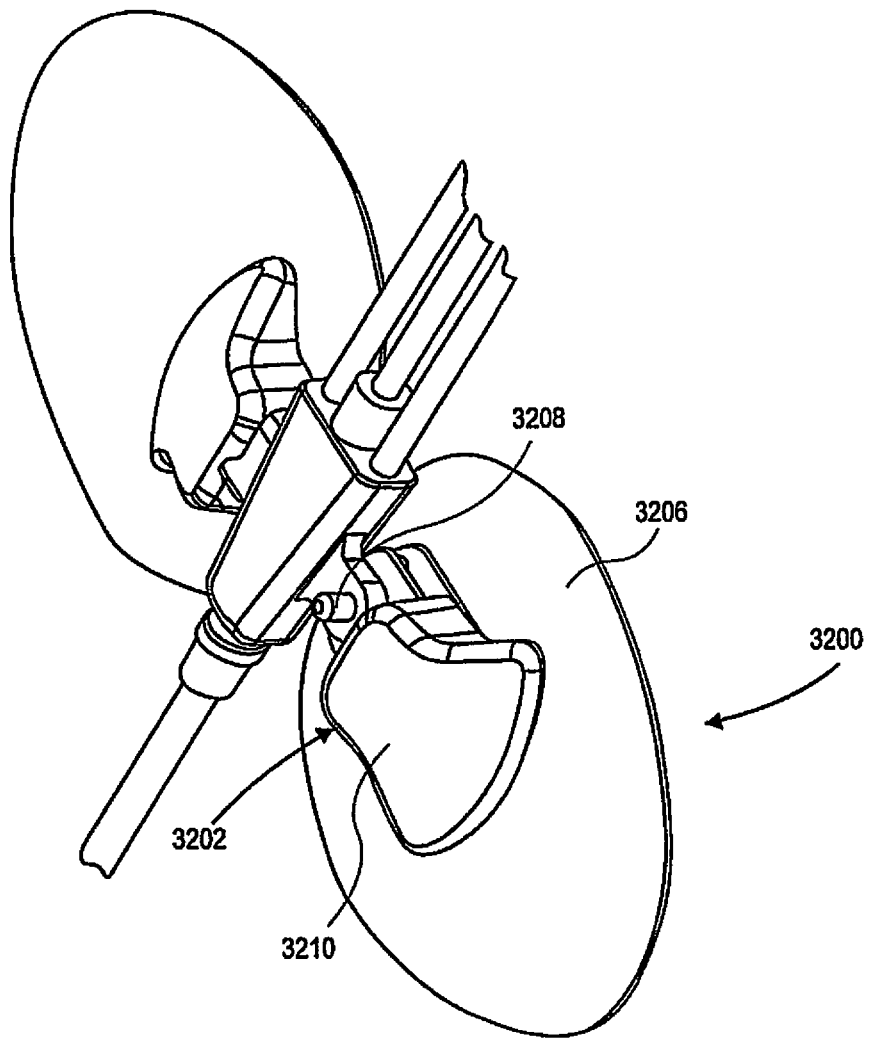

FIGS. 32A-32P illustrate another embodiment of a securement device 3200. The securement device 3200 can be modular such that the securement device 3200 can be independently attached to each suture tab on a catheter hub. The structure and use of the securement device 3200 is similar in some respects to the embodiments described above with respect to FIGS. 1-3, for example. As shown in FIGS. 32A and 32B, the securement device 3200 can include independent and modular engagement tabs 3202 that are configured to engage the suture tabs and thereby secure the catheter hub to the patient's skin. For a typical catheter with two suture tabs, the securement device 3200 includes two engagement tabs 3202. In general, the securement device 3200 has an equal number of engagement tabs 3202 as there are suture tabs. Since the engagement tabs 3202 are independent and modular, more or fewer engagement tabs 3202 can be used as needed.

The engagement tab 3202 can have a base 3204 that is attached to an adhesive pad 3206. The base can have a post 3208 sized and shaped for engaging and passing through the hole in the suture tab. The post 3208 can extend upwards from the base 3204. In some embodiments, the post 3208 can be biased away from the side of the base 3204 that faces the catheter hub, such that the distal end of the post 3208 is biased away from the suture tab when the base 3204 and post 3208 are engaged with the suture tab. The biased post 3208 aids in preventing or reducing the likelihood of accidental disengagement of the engagement tab 3202 from the suture tab when the catheter or catheter hub is pulled upwards away from the patient's skin. As the catheter or catheter hub is pulled upwards, the biased post 3208 can exert an outwards and/or downwards force on the suture tab that provides resistance to further upwards movement of the catheter or catheter hub, thereby preventing and/or resisting accidental disengagement of the engagement tab 3202 from the suture tab. In some embodiments, the post 3208 can be angled between about 0 to 30 degrees, 0 to 25 degrees, 0 to 20 degrees, or 0 to 15 degrees from the vertical axis. In some embodiments, the post 3208 is angled at least about 1, 2, 3, 4, 5, 10, 15, 20, 25, or 30 degrees from the vertical axis. In some embodiments, the post 3208 can be angled less than about 5, 10, 15, 20, 25, or 30 degrees from the vertical axis. About or approximately as used herein can mean within 10%, 20%, or 30%, for example. In some embodiments, the post 3208 can be tapered such that the distal end of the post 3208 has a smaller diameter than the proximal portion of the post 3208. In some embodiments, the post 3208 is not tapered and has a constant diameter. In some embodiments, the distal end of the post 3208 can include a barb, ball, or other retaining mechanism to improve retention of the post within the hole of the suture tab.

The engagement tab 3202 can further include a slidable cover 3210 that fits over and covers the base 3202 and the post 3208. The cover 3210 can be retracted away from the catheter hub to expose the post 3208 in an open configuration and can be advanced towards the catheter hub to cover the post 3208 in a closed configuration. The cover 3210 can be slidably mounted to the base 3202 by using, for example, a groove and rail connection between the two. For example, the cover 3210 can have two rails 3212 that fit into corresponding grooves 3214 located on the base 3202 and allow the cover to slide back and forth over the base 3202. The cover 3210 can have grip portions 3218 that protrude outwards from the cover 3210 in a direction transverse to the sliding motion of the cover 3210. The grip portions 3218 facilitate gripping and manipulation of the cover 3210 by the operator.

In some embodiments, the engagement tab 3202 can be made of a flexible or semi-rigid material that can bend or flex in response to applied stress. The added flexibility enables the engagement tab 3202 to absorb force exerted on the engagement tab 3202, thereby reducing the force exerted on the catheter and/or catheter hub which reduces the risk of accidental dislodgement of the catheter from the patient.

As illustrated in FIGS. 32C and 32D, the adhesive pad 3206 can include a peelable backing layer 3216 to cover the adhesive on the adhesive pad 3206. The backing layer 3216 can have a pull tab for removing the backing layer from the adhesive pad 3206 and thereby exposing the adhesive on the adhesive pad 3206. In some embodiments, the backing layer 3216 can be divided into multiple pieces, each with a separate tab to facilitate peeling. For example, the backing layer 3216 can have a first portion that covers the area around the base 3202 and a second portion away from base 3202. Having two portions allows only a relatively small portion of the adhesive to be exposed while positioning the securement device 3200 on the patient, which may allow easier repositioning of the securement device. In other embodiments, the backing layer 3216 can be formed of a single piece with a single tab to facilitate peeling. The backing layer 3216 can be removed before the adhesive pad 3206 is pressed into contact with the patient's skin. In some embodiments, the backing layer 3216 can be removed prior to inserting the post through the hole in the suture tab. In other embodiments, the backing layer 3216 can be removed after inserting the post through the hole in the suture tab.

In some embodiments, the adhesive pads 3206 can use a combination of an acrylic adhesive for the high stress points and a hydrocolloid adhesive for long term securement and comfort. In some embodiments, the adhesive pads 3206 can use either the acrylic adhesive or the hydrocolloid adhesive. The backing layer 3216 can be made from paper, plastic or any other suitable material that can be peeled from the adhesive. In some embodiments, a two or more securement devices 3200 can be disposed on a single backing layer 3216 that can be perforated or scored between the adhesive pads 3206 of the securement devices 3200 to allow the securement devices 3200 to be held together during packaging and easy separation of the securement devices 3200 from each other before use. The adhesive pad substrate can be a skin tone fabric or a clear material that allows for the skin color to show through in order to minimize the visual impact of the device on the patient who may have to endure the catheter for many days. The adhesive pad 3206 can be made of a flexible material so that it can conform to that geometry of the patient's body.

FIGS. 32E-32G illustrate an embodiment of the engagement tab 3202 with the backing layer removed. In addition, FIG. 32E illustrates a cross-sectional view of the engagement tab 3202 along a plane that passes through the groove 3214 and rail 3212 connection. The slidable groove and rail connection can be provided with a locking feature, such as a snap-lock feature that secures the cover 3210 over the base 3204 in the closed configuration. The snap-lock feature can be made by, for example, providing a rounded protrusion 3220 in the groove 3214 or slot and a matching or complementary rounded indentation 3222 in the rail 3212. Alternatively, the rounded protrusion 3220 can be placed on the rail 3212 and the rounded indentation 3222 can be placed on the groove 3214. In the closed configuration, the rounded protrusion 3220 is placed within the rounded indentation 3222, thereby securing the cover 3210 in place over the base 3204. The cover 3210 can be made of a flexible material such that upon the application of force, the rails 3212 can be displaced outwards to free the rails from the locked position. To return the cover 3210 back to the locked position, force can be applied to slide the rails within the slot or groove until the rounded protrusion 3220 snaps back into the rounded indentation 3222. In some embodiments, the locking feature provides a tactile and/or audible click to alert the operator that cover 3210 has been moved to the locked or unlocked configuration. In addition, the base 3204 can be made of a different color that the cover such that the operator is provided with a visual indicator of the open or close configuration of the cover 3210.

FIGS. 32H-32O illustrate various views of the cover 3210 and the base 3204. In addition to the features described above, FIGS. 32I and 32M, illustrate a stop feature that prevents the cover 3210 from sliding off the base 3204. The stop feature can also be integrated into the groove and rail connection by, for example, providing a transversely extending rail stop 3224 and a corresponding transversely extending groove stop 3226 that are designed to abut against one another to stop further movement of the cover 3210 relative to the base 3204 when the cover 3210 is at the fully opened configuration.

Because the securement device 3200 comes in modular parts, the securement device can accommodate catheter hubs of any width that uses suture tabs. This enables a universal fit for many catheter styles or brands. As described above, a modular securement device 3200 provides many benefits.

Attaching the engagement tab 3202 to the suture tab on the catheter is a simple maneuver that can be accomplished by simply engaging the post 3208 of the engagement tab 3202 with the hole of the suture tab from the bottom up, as illustrated in FIG. 32P. The post 3208 can be exposed, if covered, by retracting the cover 3210 away from the catheter as described above. This requires very little manipulation of the indwelling catheter which is a priority of users. Since the modular engagement tabs 3202 are independent, each engagement tab 3202 can be optimally positioned sequentially according to the patient anatomy. This lends flexibility of placement which is another important feature for users. In addition, in some embodiments, the fit of the post 3208 within the hole of the suture tab can leave some room for the post 3208 to pivot within the hole, which can further enhance the ability of the modular securement system to conform to the variable geometry of the patient's body. This can be accomplished, for example, by making the post 3208 have a smaller diameter than the hole of the suture tab. The ability of the engagement tabs 3202 to pivot on the suture tab allows the engagement tabs 3202 and catheter hub or other device to each lie within different planes if needed, which aids the system in conforming to the patient's body. The adhesive pads 3206 of each engagement tab 3202 can be trimmed to any shape if needed. Once both engagement tabs 3202 are in place, the catheter is held extremely well by the adhesive pads 3206. The shape and placement of adhesive provides resistance to lateral and upwards pulling of the catheter or tubing, thereby ensuring proper securement of the catheter to the patient. In addition, after the post 3208 of the engagement tab 3202 has been inserted through the suture tab, the cover 3210 can be slid back over the base 3204 and post 3208 to secure the suture tab within the engagement tab 3202. The sliding action to lock the cover 3210 in place avoids downwards pressure to close the device which can reduce unwanted motion being transmitted to the indwelling catheter.

In some embodiments, the engagement tab 3202, and particularly the cover 3210, can be dome shaped with curved surfaces. The dome can have a continuously smooth surface or a non continuous smooth surface with a flattened top portion. In some embodiments, a dome with a continuously smooth surface can be more easily covered with an overdressing such that pockets of air trapped between the overdressing and dome are reduced. The engagement tab 3202 can be made of a transparent material, such as a transparent plastic, that allows the user to visualize the post 3208 through the cover 3210. The post 3208 can be made opaque so that it is easier to visualize. For example, the post can be coated or made from an opaque material. The discrete shape and size of the dome permits full visualization of the catheter hub and skin entry point. The engagement tab 3202 can have a low profile which enables smooth placement of overdressings, such as Tegaderm™, over the catheter, catheter hub, and/or securement devices 3200. For example, the engagement tab 3202 can have a height that is less than or equal to the height of the catheter and/or the catheter hub. This results in a securement device 3200 with optional overdressing that is no higher than the catheter or catheter hub itself with no obtrusive bumps, housings, catch points and the like for maximum patient comfort while reducing the likelihood of accidentally snagging and dislodging or removing the catheter, catheter hub and/or securement device 3200.

As described above in the other embodiments, the securement device 3200 can be used to secure a variety of different catheters and be used with a variety of different adaptors and line management devices.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. For example, features described in one embodiment can be used in another embodiment. The embodiments were chosen and described in order to best explain the principles of the invention and its practical application, to thereby enable others skilled in the art to best utilize the invention and various embodiments with various modifications as are suited to the particular use contemplated.

What is claimed is:

1. A securement device for securing a medical device having a suture tab to a patient's body, the device comprising:
    an adhesive pad having a first surface coated with an adhesive and a second surface;
    a base disposed on the second surface; an upwardly extending post that extends from the base and away from the adhesive pad, wherein the post is configured to engage the suture tab; and
    a cover that is slidably attached to the base portion and configured to have a closed configuration that covers the post and an open configuration that exposes the post.

2. The device of claim 1, wherein the cover is reversibly secured to the slot by a locking mechanism.

3. The device of claim 2, wherein the base has a slot and the cover has a rail which is slidably disposed in the slot.

4. The device of claim 3, wherein the locking mechanism generates a tactile indicator when the cover is moved between the closed configuration and open configuration.

5. The device of claim 3, wherein the locking mechanism generates an audible indicator when the cover is moved between the closed configuration and open configuration.

6. The device of claim 3, wherein the locking mechanism comprises a rounded protrusion disposed within the slot and a complementary rounded indentation disposed on the rail.

7. The device of claim 3, wherein the locking mechanism comprises a rounded protrusion disposed on the rail and a complementary rounded indentation disposed within the slot.

8. The device of claim 1, further comprising a backing layer disposed over the adhesive, wherein the backing layer comprises a pull tab.

9. The device of claim 8, wherein the backing layer comprises a first portion disposed proximate the base and having a first pull tab, and a second portion disposed away from the base and having a second pull tab, wherein the first portion and the second portion are separably removable.

10. A system for securing a medical device to a patient's body, the system comprising:
    an adaptor having a first suture tab, wherein the adaptor is removably disposed over a portion of the medical device; and
    a first securement device comprising an adhesive pad having a first surface coated with an adhesive and a second surface, a base disposed on the second surface, an upwardly extending post that extends from the base and away from the adhesive pad, and a cover that is slidably attached to the base portion and configured to have a dosed configuration that covers the post and an open configuration that exposes the post, wherein, the post is disposed through the first suture tab.

11. The system of claim 10 further comprising an overdressing covering at least a portion of the first securement device, adaptor and the medical device.

12. The system of claim 10, further comprising a second securement device that is secured to a second suture tab on the adaptor, wherein the second securement device is secured independently of the first securement device.

13. The system of claim 10, wherein the adaptor comprises a channel for receiving the portion of the medical device.

14. The system of claim 10, wherein the channel comprises a deformable liner.

15. The system of claim 10, wherein the deformable liner is elastic and reversibly deformable.

16. The system of claim 10, wherein the deformable liner is made of foam.

17. A method of securing a medical device having is first suture tab to a patient's body, the method comprising:
    providing a first securement device comprising an adhesive pfd having a first surface coated with an adhesive and a second surface, a base disposed on the second surface, an upwardly extending post that extends from the base and away from the adhesive pad, and a cover that is slidably attached to the base portion and configured to have a closed configuration that covers the post and an open configuration that exposes the post;
    disposing the post through the first suture tab;
    sliding the cover to the closed configuration; and
    adhering the adhesive pad to the patient's body.

18. The method of claim 17, further comprising disposing an overdressing over at least a portion of the first securement device and medical device.

19. The method of claim 17, further comprising providing a second securement device and securing the second securement device to a second suture tab on the medical device, wherein the second securement device is secured independently of the first securement device.

* * * * *